(12) United States Patent
Joshi et al.

(10) Patent No.: US 11,286,491 B2
(45) Date of Patent: Mar. 29, 2022

(54) BIOSYNTHETIC AMYLOID-BASED MATERIALS DISPLAYING FUNCTIONAL PROTEIN SEQUENCES

(71) Applicant: President and Fellows of Harvard College, Cambridge, MA (US)

(72) Inventors: Neel Satish Joshi, Somerville, MA (US); Peter Q. Nguyen, Malden, MA (US); Anna M. Duraj-Thatte, Arlington, MA (US); Pichet Praveschotinunt, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/785,874

(22) Filed: Feb. 10, 2020

(65) Prior Publication Data

US 2020/0248190 A1    Aug. 6, 2020

Related U.S. Application Data

(63) Continuation of application No. 15/564,619, filed as application No. PCT/US2016/026161 on Apr. 6, 2016, now abandoned.

(60) Provisional application No. 62/143,560, filed on Apr. 6, 2015.

(51) Int. Cl.
| | |
|---|---|
| C12N 15/62 | (2006.01) |
| C07K 14/245 | (2006.01) |
| A61K 35/74 | (2015.01) |
| A61P 1/00 | (2006.01) |
| C07K 14/33 | (2006.01) |
| C12N 15/70 | (2006.01) |

(52) U.S. Cl.
CPC .............. *C12N 15/62* (2013.01); *A61K 35/74* (2013.01); *A61P 1/00* (2018.01); *C07K 14/245* (2013.01); *C07K 14/33* (2013.01); *C12N 15/70* (2013.01); *C07K 2317/24* (2013.01); *C07K 2319/00* (2013.01); *C12N 2800/101* (2013.01)

(58) Field of Classification Search
None
See application file for complete search history.

(56) References Cited

U.S. PATENT DOCUMENTS

| | | | |
|---|---|---|---|
| 5,762,620 | A | 6/1998 | Cartmell et al. |
| 6,864,365 | B1 | 3/2005 | White et al. |
| 8,741,417 | B2 | 6/2014 | Lee et al. |
| 9,095,558 | B2 | 8/2015 | Mayes et al. |
| 9,815,871 | B2 | 11/2017 | Joshi et al. |
| 10,550,160 | B2 | 2/2020 | Joshi et al. |
| 11,098,133 | B2 | 8/2021 | Duraj-Thatte et al. |
| 2004/0220296 | A1 | 11/2004 | Lowman et al. |
| 2010/0016549 | A1 | 1/2010 | O'Mahony et al. |
| 2011/0033389 | A1 | 2/2011 | Chen et al. |
| 2011/0108199 | A1 | 5/2011 | Miller |
| 2012/0190566 | A1 | 7/2012 | Lindquist et al. |
| 2013/0040889 | A1 | 2/2013 | Bolt et al. |
| 2013/0136697 | A1 | 5/2013 | Kannan et al. |
| 2014/0105861 | A1 | 4/2014 | March et al. |
| 2014/0302043 | A1 | 10/2014 | Whittle |
| 2014/0370013 | A1 | 12/2014 | Desjarlais et al. |
| 2015/0342893 | A1 | 12/2015 | Coulter et al. |
| 2018/0258435 | A1 | 9/2018 | Joshi et al. |
| 2020/0248190 | A1 | 8/2020 | Joshi et al. |
| 2020/0255480 | A1 | 8/2020 | Joshi et al. |

FOREIGN PATENT DOCUMENTS

| | | |
|---|---|---|
| JP | 2006/503545 A | 2/2006 |
| JP | 2008/531059 A | 8/2008 |
| JP | 2009/73766 A | 4/2009 |
| JP | 2010/515445 A | 5/2010 |
| JP | 2014/156428 A | 8/2014 |
| JP | 2014/527405 A | 10/2014 |
| KR | 2012/0060442 A | 6/2012 |
| WO | WO-2003/068934 A2 | 8/2003 |
| WO | WO-2006/096515 A2 | 9/2006 |
| WO | WO-2008/084115 A2 | 7/2008 |
| WO | WO-2011/126174 A1 | 10/2011 |
| WO | WO-2012/138570 A2 | 10/2012 |
| WO | WO-2012/166906 A1 | 12/2012 |
| WO | WO-2013/009545 A1 | 1/2013 |
| WO | WO-2013/020074 A2 | 2/2013 |
| WO | WO-2013/188529 A1 | 12/2013 |
| WO | WO-2014/018572 A2 | 1/2014 |
| WO | WO-2014018572 A2 * | 1/2014 .............. A61P 27/02 |
| WO | WO-2014/078489 A1 | 5/2014 |
| WO | WO-2014/139468 A1 | 9/2014 |
| WO | WO-2014/176311 A1 | 10/2014 |
| WO | WO-2015/080671 A1 | 6/2015 |
| WO | WO-2015/097289 A1 | 7/2015 |
| WO | WO-2016/164422 A2 | 10/2016 |

OTHER PUBLICATIONS

Hoffman et al. 2009 (Trefoil Factor Family (TFF) Peptides and Chemokine Receptors: A promising relationship; J. Med. Chem. 52: 6505-6510). (Year: 2009).*
Nash 2015 (Engineering a Functionalized Biofilm-Based Material for Modulating *Escherichia coli's* Effects in the Mammalian Gastrointestinal Tract. Bachelor's thesis, Harvard College; http://nrs.harvard.edu/urn-3:HUL.InstRepos:17417585 (Year: 2015).*
Silacci et al. 2014 (Linker length matters, Fynomer-Fc Fusion with an Optimized Linker Displaying Picomolar IL-17A inhibition Potency; Journal of Biological Chemistry, 299(20): 14392-14398) (Year: 2014).*

(Continued)

*Primary Examiner* — Mary Maille Lyons
(74) *Attorney, Agent, or Firm* — Foley Hoag LLP

(57) ABSTRACT

Methods of making biofilms having non-native functional polypeptides attached thereto are provided.

19 Claims, 7 Drawing Sheets

Specification includes a Sequence Listing.

(56) References Cited

OTHER PUBLICATIONS

Chen et al. 2013 (Fusion Protein Linkers: Property Design and Functionality; Adv Drug Deliv Rev Oct. 15; 65(10): 1357-1369) (Year: 2013).*
Chen et al., "Fusion Protein Linkers: Property, Design, and Functionality," Adv Drug Deliv Rev. 65(10): 1357-1369 (32 pages)(2013).
Chen et al., "Synthesis and patterning of tunable multiscale materials with engineered cells," Nature Materials, 13 (5): 515-23 and Supplementary Information (20 pages)(2014).
Courchesne et al., "Scalable Production of Genetically Engineered Nanofibrous Macoscopic Material via Filtration," ACS Biomater. Sci. Eng., 3: 733-741 and supporting information (2017).
Hancock et al., "Probiotic *Escherichia coli* strain Nissle 1917 outcompetes intestinal pathogens during biofilm formation," Journal of Medical Microbiology, 59(4): 392-399 (2010).
International Preliminary Report on Patentability for Application No. PCT/US2017/033579 dated Nov. 29, 2018 (20 pages).
International Search Report and Written Opinion for Application No. PCT/US2017/033579 dated Oct. 2, 2017 (22 pages).
International Search Report and Written Opinion for International Application No. PCT/US2016/026161 dated Dec. 19, 2016.
International Search Report for Application No. PCT/US2014/035095, dated Sep. 30, 2014, 5 pages.
Klein et al., "Structure-Function Analysis of the Curli Accessory Protein CsgE Defines Surfaces Essential for Coordinating Amyloid Fiber Formation," mBio, 9(4): e01349-18 (15 pages)(2018).
Lieleg et al., "Biological hydrogels as selective diffusion barriers," Trends in Cell Biology, 21(9): 543-551 (2011).
Men et al., "An auto-biotinylated bifunctional protein nanowire for ultra-sensitive molecular biosensing," Biosens Bioelectron, 26(4): 1137-41 (2010).
Nash., "Engineering a Functionalized Biofilm-Based Material for Modulating *Escherichia coli's* Effects in the Mammalian Gastrointestinal Tract," Bachelor's Thesis, Harvard College: 90 pages (2015).
Nguyen et al., "Programmable biofilm-based materials from engineered curli nanofibres," Nature Communications, 5(17): 4945 (10 pages)(2014).
Nussbaumer et al., "Bootstrapped Biocatalysis: Biofilm-Derived Materials as Reversibly Functionalizable Multienzyme Surfaces," ChemCatChem Communications, 9: 4328-4333 and supporting information (2017).
Tukel et al., "CsgA is a pathogen-associated molecular pattern of *Salmonella enterica* serotype Typhimurium that is recognized by Toll-like receptor 2," Mol Microbiol., 58(1): 289-304. (2005).
Van Gerven et al., "Secretion and functional display of fusion proteins through the curli biogenesis pathway," Mol Microbiol., 91(5): 1022-35 (2014).
Veggiani et al.. "Superglue from bacteria: unbreakable bridges for protein nanotechnology," Trends Biotechnol., 32(10): 506-12 (2014).
Wang et al., "The molecular basis of functional bacterial amyloid polymerization and nucleation," J Biol Chem., 283(31): 21530-9 (2008).
Zakeri et al., "Peptide tag forming a rapid covalent bond to a protein, through engineering a bacterial adhesin," PNAS,109: E690-E697 (2012).
Zhang et al., "Panning and Identification of a Colon Tumor Binding Peptide from a Phage Display Peptide Library," Journal of Biomolecular Screening, 12(3): 429-435 (2007).
Greenspan et al., "Defining epitopes: It's not as easy as it seems," Nature Biotechnology, 17: 936-937(1999).
Rudinger., "Characteristics of the amino acids as components of a peptide hormone sequence," Peptide Hormones: 1-7 (1976).
Skolnick et al., "From genes to protein structure and function: novel applications of computational approaches in the genomic era," Trends in Biotechnology, 18(1): 34-39 (2000).

\* cited by examiner

FIGURE 8C

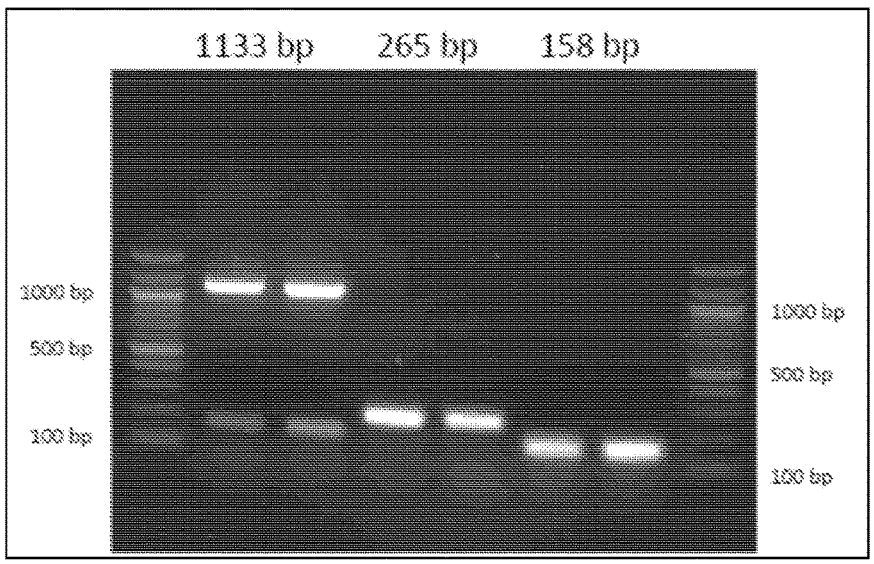

FIGURE 8D

```
NNNNNNNNNCGCANCAGANCNTTCTCTCCNGGTTCNTCTTATGCTCGATATTTCAACAAATTAAGACTTTTCTGAAGAGGGC
AGCCATTGTTGTGATAAATGAAGTGACTGTCCATCAGAAACAGTAACAACTATTTTCACCCGATCGTCCGGGGAAATATTTA
AACTCAACTTCGTCAAAGCAATGGGTTGATTAGCAGGCAATGAGAGGGTCTTTTCTTGCTTCGTCTGACTTTGCCCTGAACT
GCCTTCGCGCAGGGACAATATTTGTACTCTGCACAGACAAGATTGAGTAAGAGTGACTTCAGGAATAATGGTGTACATATCC
CCTTGCTGGGTCGTATTAAAGGTTATCTGACTGGAAAGTGCCGCAAGGAGTAATAACGCATTCATATTCTTCTCCCGAAAAA
AAACAGGGCTTGCGCCGTGTAGGCTGGAGCTGCTTCGAAGTTCCTATACTTTCTAGAGAATAGGAACTTCGGAATAGGAACT
TCATTTAAATGGCGCGCCTTACGCCCCGCCCTGCCACTCATCGCAGTACTGTTGTATTCATTAAGCATCTGCCGACATGGAA
GCCATCACAAACGGCATGATGAACCTGAATCGCCAGCGGCATCAGCACCTTGTCGCCTTGCGTATAATATTTGCCCATGGTG
AAAACGGGGCGAAGAAGTTGTCCATATTGGCCACGTTTAAATCAAAACTGGTGAAACTCACCCAGGGATTGGCTGAGACGA
AAAACATATTCTCAATAAACCCTTTAGGGAAATAGGCCAGGTTTTCACCGTAACACGCCACATCTTGCGAATATATGTGTAG
AAACTGCCGGAAATCGTCGTGGTATTCACTCCAGAGCGATGAAAACGTTTCAGTTTGCTCATGGAAAACGGTGTAACAAGGG
TGAACACTATCCCATATCACCAGCTCACCGTCTTTCATTGCCATACGTAATTCCGGATGAGCATTCATCAGGCGGGCAAGAA
TGTGAATAAAGGCCGGATAAAACTTGTGCTTATTTTTCTTTACGGTCTTTAAAAAGGCCGTAATATCCAGCTGAACGGTCTG
GTTATAGGTACATTGAGCAACTGACTGAAATGCCTCAAAATGTTCTTTACGATGCCATTGGGATATATCAACGGTGGTATAT
CCAGTGATTTTTTTCTCCATTTTAGCTTCCTTAGCTCCTGAAAATCTCGACAACTCAAAAAATACGCCCGGTAGTGATCTTA
TTTCATTATGGTGAAAGTTGGAACCTCTTACGTGCCGATCAACGTCTCATTTTCGCCAAAAGTTGGCCCAGGGCTTCCCGGT
ATCAACAGGGACACCAGGATTTATTTATTCTGCGAAGTGATCTTCCGTCACAGGTAGGCGCGCCGAAGTTCCTATACTTTCT
AGAGAATAGGAACTTCGGAATAGGAACTAAGGAGGATATTCATATGGACCATGGCTAATTCCCATGTAAAACCCCATCGGA
TTGATTTAAAAGTCGAATGGAAATTAACGTTGTGTCACGCGAATAGCCATTTGCGACTGTCTCTGCACTACAATTGCCGTTT
TTTGAGTACCATACTGTGTAATATTTGCTTTATTACCAGAACCTTTCTGGATAATCATCGCAGTATTACCATAAGCACCTTG
CGAAATACTGGCATCGTTGGCACTGCCCGCCTGATCAATATATGCAAGGTTATAATCTCCTGTCTGATCAATCTTTGCCCAG
TTGCTACTACCTTCTTGCGCAACAACCGTCAAAAGTTTTGAGCCTCCCTGCCGTAACTGAGCACTATTATTAGTCCCAGCTT
GACCAATTATGGCTGCCTGATTAAATGAAGACTTACTCAATTCATTTACCGCAAAGTTATATTCTGAATTAGCTAAATCATA
ACCTGCTGCGGCTGCAATCCCAGGCGCACCCAGTATTGTTAACATCATAAATAACAATTTGTTTTTCATGTTGTCACCCTGG
ACCTGGTCGTACNNNNNNAANNNNNNNNN    (SEQ ID NO:2)
```

BIOSYNTHETIC AMYLOID-BASED MATERIALS DISPLAYING FUNCTIONAL PROTEIN SEQUENCES

RELATED APPLICATION DATA

This application is a continuation application of U.S. application Ser. No. 15/564,619, filed Oct. 5, 2017, which is a national stage entry of PCT/US2016/026161, filed on Apr. 6, 2016, which claims priority to U.S. Provisional Application No. 62/143,560, filed on Apr. 6, 2015. The entire contents of each of the foregoing applications are hereby incorporated herein by reference in their entirety for all purposes.

The instant application contains a Sequence Listing which has been submitted electronically in ASCII format and is hereby incorporated by reference in its entirety. Said ASCII copy, created on Feb. 7, 2020, is named 117823_13003_Seq_List.txt and is 21,053 bytes in size.

STATEMENT OF GOVERNMENT INTERESTS

This invention was made with government support under DMR-1410751 awarded by the National Science Foundation. The government has certain rights in the invention.

FIELD

The technology described herein relates to engineered polypeptides, bacteria comprising such polypeptides, engineered bacteria, biofilms comprising said bacterial cells, biofilms comprising the engineered polypeptides produced by the engineered bacterial cells, and amyloid-based extracellular matrix components produced by engineered bacterial cells.

BACKGROUND

In nature, most bacteria exist as biofilm communities, residing in a self-generated protective nanoscale scaffold of proteins, sugars, lipids, and extracellular DNA that defends against environmental rigors. Biofilm formation is essential for bacterial adhesion and colonization of both natural and man-made surfaces. These highly evolved extracellular matrices hold untapped potential as a beneficial nanobiotechnology engineering platform. Biofilms have been investigated for beneficial purposes such as wastewater treatment and biotransformations, but these efforts focus on the use of naturally occurring organisms. Efforts to engineer the structure of biofilms exist. See WO/2012/166906 and PCT/US2014/035095.

SUMMARY

Embodiments of the present disclosure are directed to methods of genetically modifying bacteria to create amyloid-based materials, such as biofilms created by amyloid fibers, having non-native functional polypeptides expressed thereon and connected thereto by a linker domain optimized for functioning of the non-native functional polypeptides. According to one aspect, the linker domain is optimized for functioning of a CsgA protein as is it assembled into an amyloid state and for functioning of the functional polypeptide. Exemplary biofilms may include living bacterial cells, non-living bacterial cells or combinations of living bacterial cells and non-living bacterial cells.

Exemplary bacteria as described herein include *E. coli*. Exemplary bacteria as described herein include non-pathogenic bacteria. Exemplary bacteria as described herein include Nissle strain 1917 (EcN), MG1655, K12-derived strains, such as LSR10 and PHL628. Exemplary bacteria as described herein include bacteria that have been genetically modified to remove the nucleic acid sequence or nucleic acid sequences encoding the CsgA protein, i.e. the CsgA gene. Exemplary bacteria as described herein include bacteria that have been genetically modified to include a genomic deletion of the nucleic acid sequence or nucleic acid sequences encoding the CsgA protein, i.e., the CsgA gene. Exemplary bacteria as described herein are useful in the methods also described herein, such as the therapeutic or diagnostics methods described herein.

According to one aspect, a functional polypeptide is linked to the CsgA protein by a linker to form a CsgA-linker-functional polypeptide structure. According to one aspect, one or more nucleic acid sequences which encode for the CsgA-linker-functional polypeptide structure are included in a bacteria cell or the bacteria cell is genetically modified to include one or more nucleic acid sequences which encode for the CsgA-linker-functional polypeptide structure. The one or more nucleic acid sequences, which may be foreign nucleic acid sequences, are inserted into the bacteria using methods known to those of skill in the art and the bacteria expresses the CsgA-linker-functional polypeptide structure. According to one aspect, a naturally occurring bacteria is modified to include one or more foreign nucleic acid sequences thereby resulting in a non-naturally occurring bacteria. According to one aspect, the non-naturally occurring CsgA-linker-functional polypeptide structure is secreted and assembled to produce an amyloid nanofiber network which includes the functional polypeptide. In an exemplary embodiment, the functional polypeptide is on the surface of the amyloid nanofiber network and provides the amyloid nanofiber network with the property or characteristic of the functional polypeptide. Functional polypeptides of various lengths, secondary structures, properties, characteristics, functions, and the like are envisioned as being attached to the CsgA protein while still allowing amyloid formation and while imparting the properties, characteristics, functions of the functional polypeptide to the biofilm.

According to one aspect, an engineered bacteria is provided as is an engineered CsgA protein insofar as the CsgA protein includes the linker and the functional polypeptide and the engineered bacteria includes one or more nucleic acid sequences encoding the CsgA-linker-functional polypeptide structure. The engineered bacteria may or may not include a genomic deletion of the natural CsgA gene as described above. According to this aspect, both the engineered bacteria and the engineered CsgA protein are non-naturally occurring.

According to one aspect, the CsgA may have attached thereto two or more linkers to each of which is attached a functional polypeptide or functional group. According to one aspect, the amyloid network may include two or more CsgA species, each attached to its own linker. According to this aspect, a CsgA protein may have attached thereto two or more or a plurality of linkers each of which may or may not have a functional polypeptide or functional group attached thereto to provide a CsgA protein with a two or more or a plurality of functional polypeptides or functional groups attached thereto. Each functional polypeptide or functional group may be the same or different. For example, one functional polypeptide or group attached to the CsgA protein via a first linker may be a cell specific binding functional polypeptide or functional group and a different functional polypeptide or functional group attached to a different CsgA via a second linker may be a therapeutic or diagnostic functional polypeptide or functional group. According to this aspect, the assembled hybrid amyloid fiber, composed of the two CsgA variants can target a particular tissue or cell type and also deliver a therapeutic or diagnostic agent to the tissue or cell type. Linkers may be attached at any location of the CsgA protein as is feasible including the N-terminus, the C-terminus or at locations in between the N-terminus and the C-terminus. Further, two or more or a plurality of linker domains may be attached in series with a functional polypeptide or group attached to each linker, thereby providing two or more or a plurality of functional polypeptides or groups to the CsgA protein.

Accordingly, methods described herein include the proliferation of the bacteria cell or bacterial cells to create a population of bacteria cells that expression the foreign nucleic acid to create curli fibers and a biofilm including the functional polypeptide.

Aspects according to the present disclosure include administering the bacteria as described herein to an organism for therapeutic or diagnostic purposes. An organism includes a mammal, such as a human or a non-human mammal.

Further features and advantages of certain embodiments of the present invention will become more fully apparent in the following description of embodiments and drawings thereof, and from the claims.

BRIEF DESCRIPTION OF THE DRAWINGS

FIG. 8A-8D depict construction of a construction of a csgA deletion mutant of Nissle 1917. FIG. 8A depicts a Lambda red recombination strategy for the deletion of the csgA gene in Nissle. FIG. 8B depicts PCR validation of the chloramphenicol cassette insertion at the csgA locus identifies two positive clones (black arrows). FIG. 8C depicts these two clones were verified for the presence of the 265, 158, and 1113 bp amplicons. FIG. 8D depicts sequencing verification of the regions flanking the csgA gene indicates successful CAT cassette integration (highlighted in yellow) (SEQ ID NO:2).

DETAILED DESCRIPTION

Figure 1:
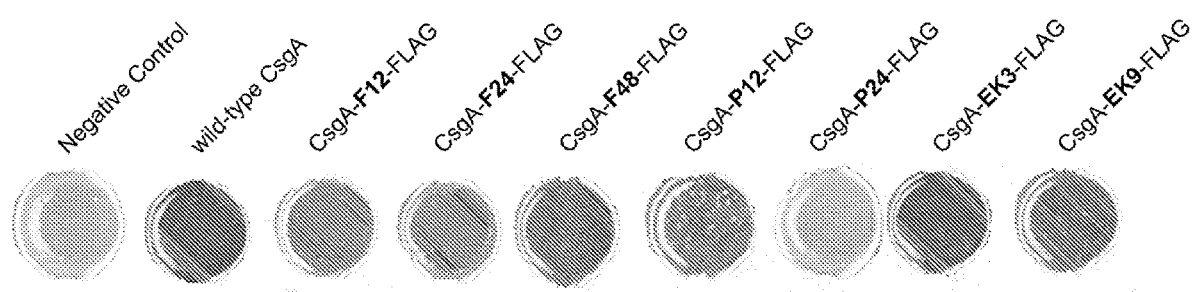
FIG. 1 depicts results of a Congo-Red plate assay where the presence of extracellular amyloid fibers is shown by red staining of the culture spots. The data was obtained from a LSR10 strain.

Aspects of the present disclosure are directed to structures having a self-assembling domain and a variable functional domain interconnected by a linker domain. According to one aspect, the self-assembling domain is a bacterial matrix protein. According to one aspect, the self-assembling domain is an amyloidogenic protein.

According to one aspect, the self-assembling domain is the amyloidogenic protein, CsgA. As used herein, "CsgA" (as distinguished from an engineered CsgA polypeptide) refers to the major structural subunit of curli. The sequences of CsgA and its homologs are known in a number of species, e.g. the sequence of *E. coli* CsgA is known (NCBI Gene ID NO: 949055; SEQ ID NO: 1 (polypeptide)).

CsgA polypeptide NCBI Ref Seq: NP_415560
1 mkllkvaaia aivfsgsala gvvpqygggg nhggggnnsg pnselniyqy gggnsalalq
61 tdarnsdlti tqhgggngad vgqgsddssi dltqrgfgns atldqwngkn semtvkqfgg
121 gngaavdqta snssvnvtqv gfgnnatahq y [SEQ ID NO:1].

In some embodiments, "CsgA" refers to *E. coli* CsgA. In some embodiments, "CsgA" refers to a polypeptide having at least 80% homology to SEQ ID NO: 1 (e.g. 80% or greater homology, 90% or greater homology, or 95% or greater homology), e.g. naturally occurring mutations or variants of CsgA, homologs of CsgA, or engineered mutations or variants of CsgA. As used herein, an "engineered CsgA polypeptide" refers to a CsgA polypeptide comprising a linker and a functional polypeptide attached to the CsgA at either the C-terminus or the N-terminus or both, but without interrupting the sequence of the CsgA polypeptide.

According to one aspect, structures according to the present disclosure include a CsgA protein, a linker and a functional polypeptide. According to one aspect, a CsgA protein is attached to a functional polypeptide by a linker. According to one aspect, the functional polypeptide is a heterologous peptide or protein domain. According to one aspect, the functional polypeptide is a heterologous peptide or protein domain that is foreign to the bacterial cell which will express the heterologous peptide or protein domain. According to one aspect, the CsgA protein, linker and functional polypeptide are attached in series, for example, having the structure CsgA-linker-functional polypeptide. According to one aspect, the CsgA protein and the functional polypeptide each exhibit functionality while bound together through the linker. According to one aspect, the combined length of the linker and functional polypeptide can be within the range of 10-500 amino acids, 10-450 amino acids, 10-400 amino acids, 10-350 amino acids or 10-300 amino acids.

According to one aspect, bacteria are modified to include a nucleic acid encoding the CsgA-linker-functional polypeptide structure. Methods of introducing a nucleic acid to a bacteria cell are known to those of skill in the art. The modified bacteria secrete the CsgA-linker-functional polypeptide structure which results in curli fiber production followed by biofilm formation. The CsgA, linker and functional protein structure are produced by engineered or non-naturally occurring bacteria and the CsgA and functional protein exhibit proper folding and exhibit functionality. According to one aspect, methods are provided for engineering a bacteria to produce a CsgA-linker-functional polypeptide structure which is exported from the bacteria and assembled into extracellular amyloid fibers. After secretion, the CsgA is nucleated to form an amyloid at the cell surface, and then continues to polymerize into long fibers that eventually encapsulate the cells and provide the biofilm with structural support. Attached to each CsgA is the linker and the functional polypeptide as a fusion. The structure is secreted and the functional polypeptide is displayed on the surface of the extracellular amyloid network. The domains are chosen such that they may have functions that can alter or enhance the properties of the biofilm as a whole and the linkers are chosen to allow the domains to have their particular functions.

Functional polypeptides within the scope of the present disclosure include peptides or proteins having a desired function. Such functions include catalytic function, recognition function or structural function. Exemplary functional polypeptides include targeting domains. Exemplary functional polypeptides include therapeutic polypeptides. Exemplary functional polypeptides include diagnostic polypeptides. Exemplary functional polypeptides include anticancer polypeptides. Exemplary functional polypeptides include antimicrobial polypeptides. Exemplary functional polypeptides include anti-inflammatory polypeptides. Exemplary functional polypeptides include polymer binding polypeptides. Exemplary functional polypeptides include metabolite binding polypeptides. Exemplary functional polypeptides include targeting polypeptides. Exemplary functional polypeptides include functional polypeptides that bind to tissues or cells or substrates. For example, by appending a domain with known steel binding capabilities to CsgA, a biofilm is produced with the ability to adhere to steel surfaces, whereas the wild-type biofilm does not have this capability. Exemplary functional polypeptides include a first member of a known binding pair. When expressed, the first member of the binding pair is available for binding to a second member of the binding pair which may have attached to it a functional polypeptide, such as for therapeutic or diagnostic purposes. In this manner, the functional polypeptide with the second member of the binding pair may be contacted to the biofilm to add the functional polypeptide to the biofilm, such as to provide the biofilm with the characteristic of the functional polypeptide. Exemplary functional polypeptides may be those to which a functional group may be covalently attached either directly or through a linker. For example, by appending to CsgA a peptide capable of undergoing spontaneous covalent modification, a biofilm whose surface can be modified with any protein or compound of interest can be created by subsequent addition of the protein or compound of interest.

Exemplary therapeutic polypeptides include engineered polypeptides with therapeutic function, polypeptides with anti-inflammatory bioactivity (trefoil factors—e.g. TFF1-3, interleukins—e.g. IL-10, other anti-inflammatory cytokines, anti-TNFα factors), polypeptides with anti-microbial bioactivity (e.g. coprisin, cathelicidin, LL-37, thuricin CD, lantibiotics), polypeptides with anti-cancer bioactivity (growth inhibiting biologics).

Exemplary diagnostic polypeptides include those known to those of skill in the art and identified by literature search.

Exemplary anticancer polypeptides include polypeptides with anti-cancer bioactivity (growth inhibiting biologics) and anticancer polypeptides include those known to those of skill in the art and identified by literature search.

Exemplary antimicrobial polypeptides include coprisin, cathelicidin, LL-37, thuricin CD, lantibiotics and antimicrobial polypeptides known to those of skill in the art and identified by literature search.

Exemplary anti-inflammatory polypeptides include trefoil factors—e.g. TFF1-3, interleukins—e.g. IL-10, other anti-inflammatory cytokines, anti-TNFα factors and anti-inflammatory polypeptides known to those of skill in the art and identified by literature search.

Exemplary polymer binding polypeptides include those known to those of skill in the art and identified by literature search.

Exemplary metabolite binding polypeptides include those known to those of skill in the art and identified by literature search.

Exemplary targeting polypeptides include those known to those of skill in the art and identified by literature search.

Exemplary tissue-binding polypeptides include T18, CP15 and those known to those of skill in the art and identified by literature search.

Exemplary cell-binding polypeptides include T18, CP15 and those known to those of skill in the art and identified by literature search.

Exemplary polypeptides that are a first pair of a binding pair of molecules include coiled-coil domains such as SynZips, Trp-Zip domains, affinity tags such as FLAG, and the like and those known to those of skill in the art and identified by literature search Linkers within the scope of the present disclosure are characterized in terms of amino acid content, length, rigidity and secondary structure. Linkers within the scope of the present disclosure separate the amyloid domain and the functional polypeptide domain and allow proper folding and functioning of each domain. In this manner, a linker can be tailored to the particular amyloid domain and the particular functional polypeptide domain. According to one aspect, functional independence of the structural (i.e., CsgA) and fused (heterologous) domains is maximized by a suitable linker to limit steric interference between domains during the export and assembly processes of the bacterial cell. According to one aspect, longer and more flexible linkers of the type (GGGS)$_n$ (SEQ ID NO:4) are exemplary. According to an additional aspect, cell stress is minimized by limiting the overall length of the fusion protein. Longer linker sequences and higher induction levels stress the biosynthetic machinery of the cells, inhibiting cell growth and leading to cell lysis in extreme cases.

Linkers within the scope of the present disclosure facilitate functioning of the CsgA domain and the functional peptide domain. Linkers within the scope of the present disclosure allow efficient protein processing and export through the bacterial curli secretion machinery as well as provide the proper spatial and physicochemical separation of the amyloid and functional domains to retain their respective functions.

Linkers within the scope of the present disclosure include amino acid residues. The amino acid residues may be any of the naturally occurring amino acid residues. Amino acid residues may also be synthetic amino acids known to those of skill in the art. Representative amino acids which may be used in linkers include Glycine, Alanine, Valine, Leucine, Isoleucine, Serine, Cysteine, Selenocysteine, Threonine, Methionine, Proline, Phenylalanine, Tyrosine, Tryptophan, Histidine, Lysine, Arginine, Aspartate, Glutamate, Asparagine, and Glutamine.

Linkers within the scope of the present disclosure include a cleavage site. Cleavage sites and enzymes for cleavage are known to those of skill in the art. According to this embodiment, the functional polypeptide may be cleaved from the linker and released into the surrounding environment, for example for therapeutic or diagnostic purposes. Exemplary enzymes include those from the family of matrix metalloproteinases (MMPs), which have their own recognition sequences, proteases secreted by pathogens such as CD2830 from *C. difficile* and the like.

CsgA within the scope of the present disclosure includes an amyloid domain which self-assembles into an amyloid structure. According to certain aspects, a linker may be attached to either the C terminus or the N-terminus or separate linkers may be attached to both the C terminus and the N terminus.

According to one aspect, the linker length can be any length which may be expressed from a cell, such as a bacterial cell when linking a CsgA protein and a functional polypeptide. According to one aspect, the functional polypeptide length can be any length which may be expressed from a cell, such as a bacterial cell when linked to a CsgA protein by a linker. According to one aspect, the combination of a linker and functional polypeptide includes no more than 500 amino acids. In some embodiments, the combination of a linker and functional polypeptide includes no more than 400 amino acids. In some embodiments, the combination of a linker and functional polypeptide includes no more than 300 amino acids. In some embodiments, the combination of a linker and functional polypeptide includes no more than 200 amino acids. In some embodiments, the combination of a linker and functional polypeptide includes no more than 100 amino acids. In some embodiments, the combination of a linker and functional polypeptide includes no more than 50 amino acids. In some embodiments, the combination of a linker and functional polypeptide includes no more than 40 amino acids. In some embodiments, the combination of a linker and functional polypeptide includes no more than 30 amino acids.

According to one aspect, a linker sequence is a polypeptide sequence of at least 7, 8, 9, 10, 11, 12, 24, 48 or more amino acids. In some embodiments, the linker sequence comprises from about 7 amino acids to about 250 amino acids. In some embodiments, the linker sequence comprises from about 7 amino acids to about 200 amino acids. In some embodiments, the linker sequence comprises from about 7 amino acids to about 150 amino acids. In some embodiments, the linker sequence comprises from about 7 amino acids to about 100 amino acids. In some embodiments, the linker sequence comprises from about 12 amino acids to about 250 amino acids. In some embodiments, the linker sequence comprises from about 12 amino acids to about 200 amino acids. In some embodiments, the linker sequence comprises from about 12 amino acids to about 150 amino acids. In some embodiments, the linker sequence comprises from about 12 amino acids to about 100 amino acids. In some embodiments, the linker sequence comprises from about 24 amino acids to about 100 amino acids. In some embodiments, the linker sequence comprises from about 48 amino acids to about 250 amino acids. In some embodiments, the linker sequence comprises from about 48 amino acids to about 200 amino acids. In some embodiments, the linker sequence comprises from about 48 amino acids to about 150 amino acids. In some embodiments, the linker sequence comprises from about 48 amino acids to about 100 amino acids. In some embodiments, the linker sequence comprises from about 7 amino acids to about 30 amino acids. In some embodiments, the linker sequence comprises from about 20 amino acids to about 50 amino acids. In some embodiments, the linker sequence comprises from about 30 amino acids to about 50 amino acids. In some embodiments, the linker sequence comprises from about 40 amino acids to about 50 amino acids. In some embodiments, the linker sequence comprises from about 6 amino acids to about 20 amino acids. In some embodiments, the linker sequence comprises from about 7 to about 10 amino acids. In some embodiments, the linker sequence comprises a flexible polypeptide, e.g a polypeptide not having a rigid secondary and/or tertiary structure. In some embodiments, the linker sequence comprises glycine and serine residues. In some embodiments at least 50% of the amino acids comprised by the linker sequence are glycine or serine residues, e.g. at least 50%, at least 60%, at least 70%, at least 80%, at least 90%, at least 95%, or more are glycine or serine residues. In some embodiments, the linker sequence consists of glycine and serine residues.

A functional polypeptide includes a polypeptide having an activity or function, such that when it is present in a biofilm, it confers upon the biofilm a property, function, or activity which it did not have in the absence of the activity of the polypeptide. Accordingly, an activity polypeptide can be, e.g. an enzyme, a polypeptide that binds another molecule, a binding domain, a peptide that is bound by another molecule (e.g. a ligand or epitope), or the like. Examples of polypeptides for use as activity polypeptides include, but are not limited to Metal binding domain (MBD); SpyTag; graphene binding (GBP); carbon nanotube binding (CBP); gold binding (A3); CT43; FLAG; Z8; E14; QBP1; CLP12; and AFP8.

According to certain aspects, the functional polypeptide when present as part of an engineered CsgA polypeptide, is functional. A polypeptide is said to be "functional" or expressed as a "functional" polypeptide if the polypeptide retains at least about 50% of the activity (e.g. enzymatic activity or binding activity) that it has as an isolated polypeptide. One of skill in the art can readily detect increases in reaction products and/or detect decreases in reaction substrates, e.g. by mass spectroscopy (MS, including, e.g., MADLI/TOF, SELDI/TOF, LC-MS, GC-MS, HPLC-MS, etc., among others) or detect increases or decrease in binding to a binding partner, e.g. by immunoassays. In some embodiments, a functional activity polypeptide can retain at least 50% of the activity of the isolated polypeptide, e.g. 50% or more of the activity, 60% or more of the activity, 75% or more of the activity, or 90% or more of the activity of the isolated polypeptide.

In some embodiments, the functional polypeptide can be a conjugation domain. Such embodiments can permit immobilization of target proteins in the biofilm, e.g., when the target protein is too large to be expressed as a fusion with CsgA. The conjugation domain present on the engineered CsgA polypeptide can specifically bind to a partner conjugation domain present as part of the target protein, thereby incorporating the target protein into the biofilm. Such conjugation domains are also referred to herein as a first member of a binding pair of molecules and a second member of a pair of binding pair of molecules. As used herein, "conjugation domain" includes a polypeptide that can specifically bind to and/or be specifically bound by a partner conjugation domain, e.g. under conditions suitable for growth of a biofilm. A conjugation domain can be, e.g., about 100 amino acids or less in size, about 75 amino acids or less in size, about 50 amino acids or less in size, about 40 amino acids or less in size or smaller. A partner conjugation domain can be about the same size as the conjugation domain or larger, e.g., a partner conjugation domain can be about 4000 amino acids or less in size, about 3000 amino acids or less in size, about 2000 amino acids or less in size, about 1000 amino acids or less in size, about 500 amino acids or less in size, about 200 amino acids or less in size, about 100 amino acids or less in size, about 75 amino acids or less in size, about 50 amino acids or less in size, about 40 amino acids or less in size, or smaller. In some embodiments, the binding of the conjugation domain and partner conjugation domain is covalent. Examples of conjugation domains are known in the art and include, but are not limited to, SpyTag; biotin acceptor peptide (BAP); biotin carboxyl carrier protein (BCCP); and a peptide comprising a LPXTG (SEQ ID NO:30) motif. Similarly, partner conjugation domains are known in the art and include but are not limited to, respectively, SpyCatcher, streptavidin; streptavidin; and peptides comprising aminoglycine. Further discussion of conjugation systems comprising a conjugation domain and a partner conjugation domain can be found, e.g., in Mao et al. J Am Chem Soc 2004 126:2670-1; Zakeri et al. PNAS 2012 109:E690-E697; and Maeda et al. Appl Environ Microbil 2008 74:5139-5145; each of which is incorporated by reference herein in its entirety.

Where the functional polypeptide is a conjugation domain, the target polypeptide comprising the partner conjugation domain can further comprise a functional agent. The functional agent has an activity or function, such that when it is present in a biofilm, it confers upon the biofilm a property, function, or activity which it did not have in the absence of the polypeptide. A functional agent can be of any size and is not part of the engineered CsgA polypeptide. Exemplary functional agents include, e.g. an enzyme, a polypeptide that binds another molecule, an antibody, a therapeutic agent, a diagnostic agent, a metal, an antimicrobial agent, an anti-inflammatory agent, an anticancer agent or the like. In some embodiments, a polypeptide comprising a functionalizing polypeptide and a conjugation domain can further comprise an extracellular localization tag, e.g. a sequence which will cause a cell expressing the polypeptide to secrete the polypeptide.

A functionalized engineered CsgA polypeptide or functionalized biofilm can be provided by contacting an engineered CsgA polypeptide comprising a conjugation domain (or a cell and/or biofilm comprising that polypeptide) with a polypeptide comprising the partner conjugation domain. In some embodiments, the engineered CsgA polypeptide and the polypeptide comprising the partner conjugation domain are maintained in contact for a period of time, i.e. the "binding step." In some embodiments, the binding step is followed by a washing step, e.g. to remove excess unbound polypeptide.

In some embodiments, an engineered CsgA polypeptide comprising a conjugation domain is bound to (or binds) the partner conjugation domain in the presence of albumin (i.e. the "binding step"). In some embodiments, the albumin is BSA. In some embodiments, the albumin is present at about 0.1% to about 10%. In some embodiments, the albumin is present at about 0.5% to about 5%. In some embodiments, the albumin is present at about 1% to about 2%. In some embodiments, the binding step is allowed to proceed for at least about 2 hours, e.g. about 2 hours or more, about 6 hours or more, about 12 hours or more, or about 24 hours or more. In some embodiments, the binding step is allowed to proceed in the presence of albumin.

In some embodiments, the washing step proceeds for about 10 minutes to about 6 hours. In some embodiments, the washing step proceeds for about 30 minutes to about 3 hours. In some embodiments, the washing step proceeds for about 90 minutes. In some embodiments, the polypeptides are agitated (e.g. shaken) during the washing step. In some embodiments, the washing step comprises washing the polypeptides in a solution of albumin. In some embodiments, the albumin is BSA. In some embodiments, the albumin is present at about 0.01% to about 3%. In some embodiments, the albumin is present at about 0.1% to about 1%. In some embodiments, the albumin is present at about 0.3%. In some embodiments, the washing step comprises 2 or more successive washes. In some embodiments, the washing step comprises 3 successive washes.

"Specific binding" includes a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In one aspect, described herein is a nucleic acid sequence encoding an engineered CsgA polypeptide as described herein. In one aspect, described herein is a vector comprising a nucleic acid sequence encoding an engineered CsgA polypeptide as described herein. A "vector" includes a nucleic acid construct designed for delivery to a host cell or transfer between different host cells. A vector can be viral or non-viral. Many vectors useful for transferring genes into target cells are available, e.g. the vectors may be episomal, e.g., plasmids, virus derived vectors or may be integrated into the target cell genome, through homologous recombination or random integration. In some embodiments, a vector can be an expression vector. An "expression vector" can be a vector that has the ability to incorporate and express heterologous nucleic acid fragments in a cell. An expression vector may comprise additional elements, for example, the expression vector may have two replication systems, thus allowing it to be maintained in two organisms. The nucleic acid incorporated into the vector can be operatively linked to an expression control sequence when the expression control sequence controls and regulates the transcription and translation of that polynucleotide sequence.

In some embodiments, a nucleic acid encoding an engineered CsgA polypeptide can be present within a portion of a plasmid. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK+/- or KS+/- (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," Gene Expression Technology, vol. 185 (1990), which is hereby incorporated by reference in its entirety).

A "viral vector" may be a nucleic acid vector construct that includes at least one element of viral origin and has the capacity to be packaged into a viral vector particle. The viral vector can contain a transgenic gene in place of non-essential viral genes. The vector and/or particle may be utilized for the purpose of transferring any nucleic acids into cells either in vitro or in vivo. Numerous viral vectors are known in the art and can be used as carriers of a nucleic acid into a cell, e.g. lambda vector system gt11, gt WES.tB, Charon 4.

In some embodiments, the nucleic acid encoding an engineered CsgA polypeptide can be constitutively expressed. In some embodiments, the nucleic acid encoding an engineered CsgA polypeptide can be operably linked to a constitutive promoter. In some embodiments, the nucleic acid encoding an engineered CsgA polypeptide can be inducibly expressed. In some embodiments, the nucleic acid encoding an engineered CsgA polypeptide can be operably linked to an inducible promoter. In some embodiments, the nucleic acid encoding an engineered CsgA polypeptide can be operably linked to a native CsgA promoter.

An "inducible promoter" may be one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g. the beta.-lactamase and lactose promoter systems (Chang et al., Nature, 275: 615 (1978, which is incorporated herein by reference); Goeddel et al., Nature, 281: 544 (1979), which is incorporated herein by reference), the arabinose promoter system, including the araBAD promoter (Guzman et al., J. Bacteriol., 174: 7716-7728 (1992), which is incorporated herein by reference; Guzman et al., J. Bacteriol., 177: 4121-4130 (1995), which is incorporated herein by reference; Siegele and Hu, Proc. Natl. Acad. Sci. USA, 94: 8168-8172 (1997), which is incorporated herein by reference), the rhamnose promoter (Haldimann et al., J. Bacteriol., 180: 1277-1286 (1998), which is incorporated herein by reference), the alkaline phosphatase promoter, a tryptophan (trp) promoter system (Goeddel, Nucleic Acids Res., 8: 4057 (1980), which is incorporated herein by reference), the PLtetO-1 and Pladare-1 promoters (Lutz and Bujard, Nucleic Acids Res., 25: 1203-1210 (1997), which is incorporated herein by reference), and hybrid promoters such as the tac promoter. deBoer et al., Proc. Natl. Acad. Sci. USA, 80: 21-25 (1983), which is incorporated herein by reference.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

In one aspect, described herein is an engineered microbial cell comprising an engineered CsgA polypeptide and/or comprising a vector or nucleic acid encoding such a polypeptide.

In some embodiments, the engineered CsgA polypeptide can comprise a functional polypeptide comprising a conjugation domain. In some embodiments, a cell encoding and/or comprising an engineered CsgA polypeptide can comprise an activity polypeptide comprising a conjugation domain can further encode and/or comprise a second engineered polypeptide comprising a partner conjugation domain and a functionalizing polypeptide. In some embodiments, described herein is a population of cells comprising two cell types, the first cell type encoding and/or comprising an engineered CsgA polypeptide comprising an activity polypeptide comprising a conjugation domain and the second cell type encoding and/or comprising a second engineered polypeptide comprising a partner conjugation domain and a functionalizing polypeptide. That is, it is contemplated herein that a single cell can comprise a CsgA polypeptide with a conjugation domain and also comprise the polypeptide which will bind to and/or be bound by that CsgA polypeptide or that a first cell can comprise a CsgA polypeptide with a conjugation domain and a second cell can comprise the polypeptide which will bind to and/or be bound by that CsgA polypeptide. It is further contemplated that an engineered CsgA polypeptide with a conjugation domain can be contacted with a second polypeptide comprising a partner conjugation domain and a functionalizing polypeptide, e.g. the second polypeptide can be produced (e.g. by a bacteria or eukaryotic cell) and/or synthesized (and optionally isolated or purified) and then brought in contact with the engineered CsgA polypeptide, e.g. when the CsgA polypeptide is present on a cell surface and/or present in a biofilm.

A bacterial cell of the methods and compositions described herein can be any of any species. Preferably, the bacterial cells are of a species and/or strain which is amenable to culture and genetic manipulation. In some embodiments, the bacterial cell can be a gram-positive bacterial cell. In some embodiments, the bacterial cell can be a gram-negative bacterial cell. In some embodiments, the parental strain of the bacterial cell of the technology described herein can be a strain optimized for protein expression. Non-limiting examples of bacterial species and strains suitable for use in the present technologies include *Escherichia coli*, *E. coli* BL21, *E. coli* Tuner, *E. coli* Rosetta, *E. coli* JM101, and derivatives of any of the foregoing. Bacterial strains for protein expression are commercially available, e.g. EXPRESS™ Competent *E. coli* (Cat. No. C2523; New England Biosciences; Ipswich, Mass.). In some embodiments, the cell is an *E. coli* cell.

In some embodiments, the nucleic acid encoding an engineered CsgA polypeptide is comprised by a cell expressing wild-type CsgA. In some embodiments, the nucleic acid encoding an engineered CsgA polypeptide is comprised by a cell with a mutation and/or deletion of the wild-type CsgA gene, e.g. such that the cell does not express wild-type CsgA. In some embodiments, the nucleic acid encoding an engineered CsgA polypeptide is introduced into a cell by homologous recombination, e.g. such that the nucleic acid encoding an engineered CsgA polypeptide replaces the wild-type CsgA gene in the cell.

In one aspect, described herein is a biofilm comprising an engineered microbial cell comprising one or more engineered CsgA polypeptides and/or comprising a vector or nucleic acid encoding such a polypeptides. As used herein, a "biofilm" refers to a mass of microorganisms which can adhere or is adhering to a surface. A biofilm comprises a matrix of extracellular polymeric substances, including, but not limited to extracellular DNA, proteins, glyopeptides, and polysaccharides. The nature of a biofilm, such as its structure and composition, can depend on the particular species of bacteria present in the biofilm. Bacteria present in a biofilm are commonly genetically or phenotypically different than corresponding bacteria not in a biofilm, such as isolated bacteria or bacteria in a colony.

In some embodiments, the technology described herein relates to a biofilm that is produced by culturing an engineered microbial cell comprising an engineered CsgA polypeptide (and/or comprising a vector or nucleic acid encoding such a polypeptide) under conditions suitable for the production of a biofilm. Conditions suitable for the production of a biofilm can include, but are not limited to, conditions under which the microbial cell is capable of logarithmic growth and/or polypeptide synthesis. Conditions may vary depending upon the species and strain of microbial cell selected. Conditions for the culture of microbial cells are well known in the art. Biofilm production can also be induced and/or enhanced by methods well known in the art, e.g. contacting cells with subinhibitory concentrations of beta-lactam or aminoglycoside antibiotics, exposing cells to fluid flow, contacting cells with exogenous poly-N-acetylglucosamine (PNAG), or contacting cells with quorum sensing signal molecules. In some embodiments, conditions suitable for the production of a biofilm can also include conditions which increase the expression and secretion of CsgA, e.g. by exogenously expressing CsgD.

In some embodiments, the biofilm can comprise the cell which produced the biofilm. In some embodiments, described herein is a composition comprising an engineered CsgA polypeptide as described herein.

When expressed by a cell capable of forming curli, e.g. a cell expressing CsgA, CsgB, CsgC, CsgD, CsgE, CsgF, and CsgG or some subset thereof, CsgA units will be assembled to form curli filaments, e.g. polymeric chains of CsgA. In some embodiments, filaments of the polypeptide can be present in the composition. In some embodiments, the filaments can be part of a proteinaceous network, e.g. multiple filaments which can be, e.g. interwoven, overlapping, and/or in contact with each other. In some embodiments, the proteinaceous network can comprise additional biofilm components, e.g. materials typically found in an *E. coli* biofilm. Non-limiting examples of biofilm components can include biofilm proteins (e.g. FimA, FimH, Ag43, AidA, and/or TibA) and/or non-proteinaceous biofilm components (e.g. cellulose, PGA and/or colonic acid). In some embodiments, the composition can further comprise an engineered microbial cell comprising an engineered CsgA polypeptide and/or comprising a vector or nucleic acid encoding such a polypeptide.

In one aspect, described herein is the use of a cell, composition, or biofilm comprising an engineered CsgA polypeptide (and/or comprising a vector or nucleic acid encoding such a polypeptide) to display a polypeptide, e.g. within the biofilm, within the composition, and/or on the cell surface. As used herein, "display" refers to expressing the polypeptide (e.g. as an activity polypeptide) in such a manner that it can come in contact with the extracellular environment. A displayed polypeptide can be capable of binding with a binding partner, catalyzing an enzymatic reaction, and/or performing any other activity which it would perform as an isolated polypeptide.

It is contemplated herein that a polypeptide displayed within a biofilm (e.g. an activity polypeptide and/or functionalizing polypeptide) will retain more activity than a soluble version of that polypeptide. It is contemplated herein that a polypeptide displayed within a biofilm (e.g. an activity polypeptide and/or functionalizing polypeptide) will retain more activity than a soluble version of that polypeptide when exposed to activity degrading conditions such as, e.g., high or low pH, organic solvents, desiccation, high or low temperature, radiation, etc.

In one aspect, described herein is the use of a cell, composition, or biofilm comprising an engineered CsgA polypeptide (and/or comprising a vector or nucleic acid encoding such a polypeptide), in an application selected from the group consisting of biocatalysis; industrial biocatalysis; immobilized biocatalysis; chemical production; filtration; isolation of molecules from an aqueous solution; water filtration; bioremediation; nanoparticle synthesis; nanowire synthesis; display of optically active materials; biosensors; surface coating; therapeutic biomaterial; biological scaffold; structural reinforcement of an object; and as a delivery system for therapeutic agents. Exemplary, non-limiting embodiments of such applications and specific activity polypeptides for use therein are described in the Examples herein.

It is contemplated herein that a cell, composition and/or biofilm can comprise multiple different engineered CsgA polypeptides, each of which comprises a different activity polypeptide, e.g. an engineered CsgA polypeptide comprising an enzymatic activity polypeptide and an engineered CsgA polypeptide comprising a binding domain activity polypeptide. A cell, composition, and/or biofilm can comprise 1 or more engineered CsgA polypeptides, e.g. 1, 2, 3, 4, 5, 6, or more engineered CsgA polypeptides.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

Linker Design

A test amyloid chimeric protein library was constructed to test various linker designs between an amyloid domain (CsgA) and a functional peptide domain (FLAG). The CsgA protein is secreted by the bacterium *Escherichia coli* and the protein then self-assembles into highly robust functional amyloid nanofibers with a diameter of ~4-7 nm. These amyloid fibers are known as 'curli' and exist as extended tangled networks encapsulating the cells. The FLAG domain is an octapeptide polypeptide tag used for affinity chromatography and epitope-tagged protein detection.

Six different domains were designed as linkers connecting the CsgA and FLAG domains as set forth in Table 1 below.

According to one aspect, a linker may be flexible or rigid. A linker may include one or more or a plurality of repeating amino acid subunits.

According to one aspect, a linker may be hydrophobic or hydrophilic.

According to one aspect, a linker may include 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or greater amino acid subunits. According to one aspect, a linker may include 2 repeating subunits or more, 3 repeating subunits or more, 4 repeating subunits or more, 5 repeating subunits or more, 6 repeating subunits or more, 7 repeating subunits or more, 8 repeating subunits or more, 9 repeating subunits or more, 10 repeating subunits or more, 11 repeating subunits or more, 12 repeating subunits or more, 13 repeating subunits or more, 14 repeating subunits or more, or 15 repeating subunits or more. According to one aspect, a plurality of amino acid subunits results in a flexible linker. A flexible linker may include a linker with a sequence that lacks inherent secondary or tertiary structure in solution. According to one aspect, a plurality of amino acid subunits results in a rigid linker. A rigid linker may include a linker with a sequence

| Plasmid Name | Linker Description | Linker | Full Sequence |
|---|---|---|---|
| pBbE1a-CsgA-F12-FLAG | Flexible [GGGS]x3 | F12 | GGGSGGGSGGGS (SEQ ID NO: 5) |
| pBbE1a-CsgA-F24-FLAG | Flexible [GGGS]x6 | F24 | GGGSGGGSGGGSGGGSGGGSGGGS (SEQ ID NO: 6) |
| pBbE1a-CsgA-F48-FLAG | Flexible [GGGS]x12 | F48 | GGGSGGGSGGGSGGGSGGGSGGGSGGGSGGGSGGGSGGGSGGGSGGGS (SEQ ID NO: 7) |
| pBbE1a-CsgA-Pro12-FLAG | PolyProline [P]x12 | P12 | PPPPPPPPPPPP (SEQ ID NO: 8) |
| pBbE1a-CsgA-Pro24-FLAG | PolyProline [P]x24 | P24 | PPPPPPPPPPPPPPPPPPPPPPPP (SEQ ID NO: 9) |
| pBbE1a-CsgA-EK3-FLAG | alpha-Helical [EAAAK]x3 | EK3 | EAAAKEAAAKEAAAK (SEQ ID NO: 10) |
| pBbE1a-CsgA-EK9-FLAG | alpha-Helical [EAAAK]x9 | EK9 | EAAAKEAAAKEAAAKEAAAKEAAAKEAAAKEAAAKEAAAKEAAAK (SEQ ID NO: 11) |

According to one aspect, a linker may include from between 7 and 50 amino acids. According to one aspect, a linker may include from between 8 and 50 amino acids. According to one aspect, a linker may include from between 9 and 50 amino acids. According to one aspect, a linker may include from between 10 and 50 amino acids. According to one aspect, a linker may include from between 11 and 50 amino acids. According to one aspect, a linker may include from between 12 and 50 amino acids. According to one aspect, a linker may include from between 15 and 50 amino acids. According to one aspect, a linker may include from between 20 and 50 amino acids. According to one aspect, a linker may include from between 24 and 50 amino acids. According to one aspect, a linker may include from between 45 and 50 amino acids.

that has a secondary or tertiary structure that allows it to maintain a defined conformation in solution.

An exemplary amino acid subunit is GGGS (SEQ ID NO:4). According to one aspect, a linker has the structure $[GGGS]_n$ where n is an integer from 1 to 20 (SEQ ID NO:12). Exemplary values for n include 3, 6, and 12. According to one aspect, a linker having a plurality of GGGS (SEQ ID NO:4) subunits is a linker that is flexible in whole or in part.

An exemplary amino acid subunit is P. According to one aspect, a linker has the structure $[P]_n$ where n is an integer from 1 to 30 (SEQ ID NO:13). According to one aspect, linkers with repetitive Ps include extended type II trans helices. Exemplary values for n include 12 and 24. According to one aspect, a linker having a plurality of P subunits is a linker that is rigid in whole or in part.

An exemplary amino acid subunit is an alpha-helix motif such as EAAAK (SEQ ID NO:14). According to one aspect, a linker has the structure [EAAAK]$_n$ where n is an integer from 1 to 15 (SEQ ID NO:15). Exemplary values for n include 3 and 9. According to one aspect, a linker having a plurality of EAAAK (SEQ ID NO:14) subunits is a linker that is rigid in whole or in part and includes a hydrophilic portion and a hydrophobic portion.

Exemplary amino acid residues include 12 or more amino acids, 24 or more amino acids or 48 or more amino acids. According to one aspect, the amino acids are flexible amino acids. According to one aspect, the amino acids are one or more of glycine, serine, alanine or leucine. According to one aspect, a corresponding increase in extracellular curli fibers results from increased linker length. According to one aspect, a corresponding increase in functional domain accessibility results from increased linker length.

Exemplary linkers include:

```
                                               (SEQ ID NO: 16)
GGGSGGGSGGGS, (SEQ ID NO: 16)
GGGSGGGSGGGSGGGSGGGSGGGS, (SEQ ID NO: 16)
GGGSGGGSGGGSGGGSGGGSGGGSGGGSGGGSGGGSGGGSGGGSGGGS (SEQ ID NO: 17)
PPPPPPPPPPPP, (SEQ ID NO: 17)
PPPPPPPPPPPPPPPPPPPPPPPP, (SEQ ID NO: 18)
EAAAKEAAAKEAAAK,
or
                                               (SEQ ID NO: 18)
EAAAKEAAAKEAAAKEAAAKEAAAKEAAAKEAAAKEAAAKEAAAK.
```

EXAMPLE II

Analysis of Amyloid Nanofiber Production

CsgA-linker-FLAG chimeras with different intervening linkers were tested for optimal self-assembly into curli nanofibers. The self-assembly of the protein library with different linkers into curli nanofibers was detected using Congo Red (CR), a standard stain used for the colorimetric detection of amyloids. Only E. coli cells expressing fusion proteins that are successfully secreted and are competent for self-assembly into amyloid nanofibers will stain red. As shown in FIG. 1, all the flexible linkers (F12, F24, and F48) show some intermediate levels of CR staining, with the longest linker showing the greatest amount. For the rigid linkers, the longer polyproline linker showed no CR staining and the highest amount of CR staining was obtained for the EK3 linker. A trend is seen for the polyproline and EAAAK (SEQ ID NO:14) linkers with the longer rigid linkers resulting in less staining. It is to be understood that this is a representative embodiment only and that a polyproline linker having 24 prolines may be a useful linker for a given functional polypeptide.

EXAMPLE III

Determination of Peptide Domain Functionality

Figure 2:
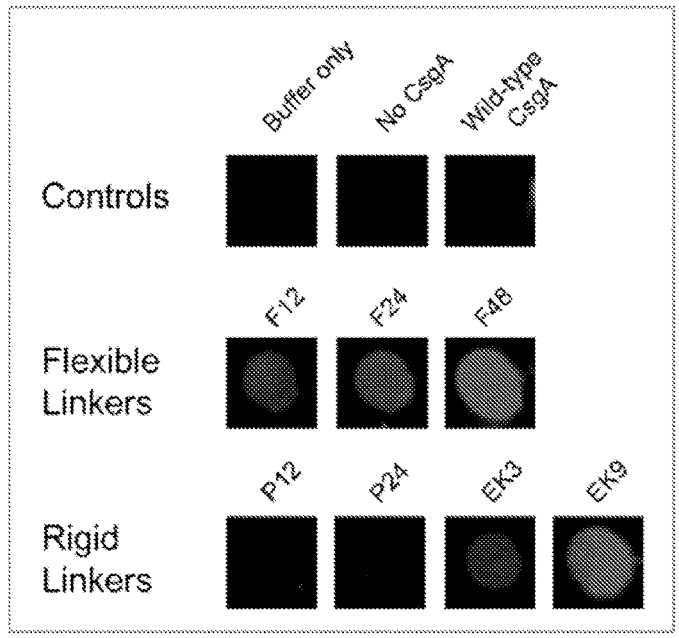
FIG. 2 depicts results of a whole-cell immunodotblot analysis for FLAG tag functionality. Accessible FLAG epitopes on CsgA-FLAG chimeras with different linker domains were probed using anti-FLAG antibodies conjugated to fluorescent DyLight 680. The data was obtained from a LSR10 strain.

To determine if the FLAG epitope tag is accessible and can properly perform its prescribed function, which is binding to an anti-FLAG antibody, immunoblot analysis of whole-cell culture samples was performed. The CsgA-linker-FLAG structure with a flexible linker demonstrated a monotonic increase in fluorescence as a function of the linker length. The CsgA-linker-FLAG structure with a polyproline rigid linker lacked fluorescence. Without wishing to be bound by scientific theory, these hydrophobic linkers may impede proper functioning of the peptide tag. The CsgA-linker-FLAG structure with an alpha-helical EAAAK (SEQ ID NO:14) linker showed that the EK3 linker construct, which had more CR staining than the EK9 construct (see FIG. 1), had lower fluorescence. In contrast, the lower CR-binding EK9 linker construct had a high fluorescent signal, indicating greater accessibility of the FLAG epitope tag. See FIG. 2.

EXAMPLE IV

Method of Optimizing Linker Design

Figure 3:
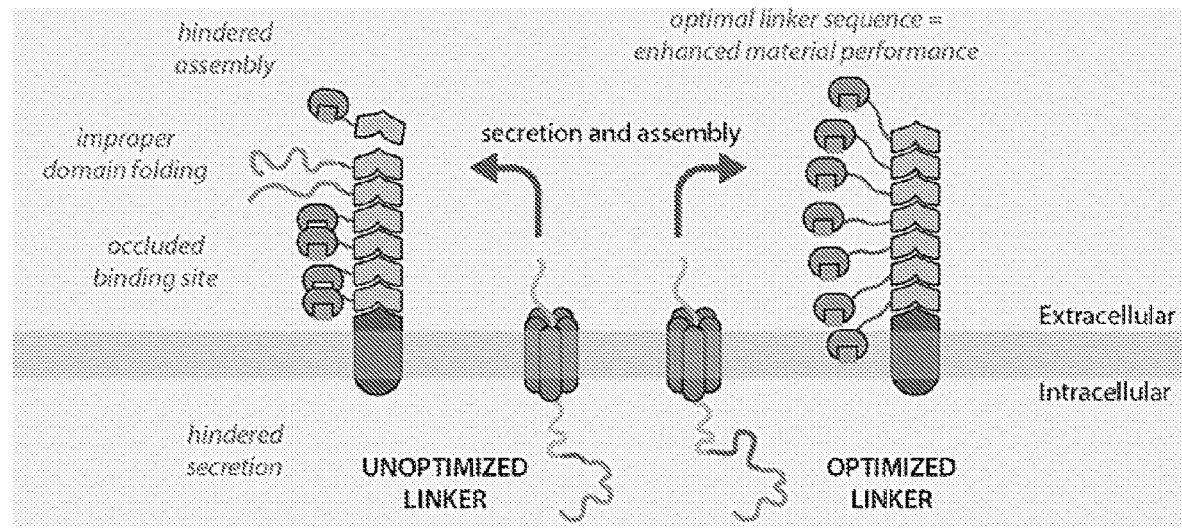
FIG. 3 depicts in schematic a strategy for optimized linker design showing the effect of optimized linker on functional polypeptide ("material") performance. Unoptimized linker domains may hinder the performance of the biofilm-based material by occluding binding sites for the functional domains, preventing proper folding of either domain, hindering assembly of the amyloid fibers, or hindering secretion. Optimized linkers minimize these issues, thereby improving the desired function of the material overall.

Aspects of the present disclosure are directed to methods of optimizing linker design for linking CsgA and a functional polypeptide. According to this aspect, a functional polypeptide is selected for linkage with CsgA. A linker design is then selected to form the CsgA-linker-functional polypeptide structure. A bacteria is then modified to include a nucleic acid sequence encoding the CsgA-linker-functional polypeptide structure. The modified bacteria may then be caused to proliferate into a population of bacteria and is assayed for the expression of the CsgA-linker-functional polypeptide structure. The modified bacteria may then be caused to proliferate into a population of bacteria and is assayed for the formation of a biofilm of the CsgA-linker-functional polypeptide structure. The biofilm may be assayed for the functional characteristics of the functional polypeptide. Accordingly, exemplary linkers described herein allow the self-assembly and functional domains of the CsgA-linker-functional polypeptide structure to operate or function without interfering with each other. An exemplary method of determining the effect of a linker on biofilm formation and functional characteristics of the functional polypeptide is depicted in FIG. 3. Unoptimized linker domains may hinder the performance of the biofilm-based material by occluding binding sites for the functional domains, preventing proper folding of the CsgA or functional polypeptide domains, hindering assembly of amyloid fibers or hindering secretion. Optimized linkers minimize these issues and improve the desired function of the biofilm. Optimized linker domains facilitate the fabrication of biofilm based materials with superior mechanical and biophysical stability under a wide range of conditions (extreme temperatures, extreme pH, in the presence of unfavorable solvents, under exposure to the elements in outdoor applications, etc.). Optimized linker domains enable each functional peptide domain to operate independently, effectively increasing the number of functional peptide domains in the material that are contributing to a desired behavior on the micro- or macro-scale. For example, if the desired function of the biofilm-based material is metal binding, the material may have inhibited stability or metal binding affinity because of molecular crowding or undesirable molecular interactions that result from inappropriate linker domains. Optimized linker domains reduce undesirable molecular interactions from occurring, ultimately enhancing the performance of the material.

EXAMPLE V

Gut Epithelial Binding

Aspects of the present disclosure are directed to methods of using engineered bacteria to create a biofilm having a heterologous domain that binds to specific tissues or cells whether healthy or diseased. According to one aspect, the bacteria is a non-pathogenic bacteria. Exemplary non-pathogenic bacteria include Nissle strain 1917 (EcN), MG1655, K12-derived strains, PHL628, LSR10, LSR6 and the like. Wild-type EcN, which is marketed as a probiotic under the trade name Mutaflor, can be delivered orally, survive transit through the upper GI tract, then transiently colonize the ileum and colon for several days after initial administration. During this colonization process, EcN produces curli fibers.

Exemplary binding domains include those identified in Table 2 below.

Functional polypeptides include a polypeptide or protein sequence that displays binding affinity with the epithelial surfaces of the gastrointestinal (GI) tract. Exemplary polypeptide or protein sequences are known to those of skill in the art or can be determined from phage display on biological tissues, from sequences that exist in naturally occurring organisms or from sequences that have been engineered in some other way to bind to specific surfaces. For example, exemplary polypeptide or protein sequences having affinity with tissues or cells associate with the GI tract can be determined from a microfluidic system that mimics the structure of a gut epithelium. Such systems may be referred to as a "Gut on a CHIP." Such systems incorporate flow and cyclic strain motions to mimic peristalsis. Engineered bacteria strains as described herein having gut binding functional groups may be introduced into such a system and the micro-scale localization and residence time in the system may be monitored to determine binding of the cells through

| Name | Sequence | Origin | Function |
|---|---|---|---|
| CP15 | VHLGYAT (SEQ ID NO: 19) | Phage Display | Binds Colon Carcinomas |
| P8 | LETTCASLCYPS (SEQ ID NO: 20) | Phage Display | Binds M cells |
| A1 | VRPMPLQ (SEQ ID NO: 21) | Phage Display | Binds Colon Carcinomas |
| T18 | LTHPQDSPPASA (SEQ ID NO: 22) | Phage Display | Binds Injured Epithelium |
| TFF1 | EAQTETCTVAPRERQNCGFPGVTPSQCANKGCCFDDTV RGVPWCFYPNTIDVPPEEECEF (SEQ ID NO: 39) | Trefoil Factor | Anti-inflammatory Binds mucosa |
| TFF2 | EKPAACRCSRQDPKNRVNCGFPGITSDQCFTSGCCFDSQ VPGVPWCFKPLPAQESEECVMQVSARKNCGYPGISPED CAARNCCFSDTIPEVPWCFFPMSVEDCHY (SEQ ID NO: 23) | Trefoil Factor | Anti-inflammatory Binds mucosa |
| TFF3 | EEYVGLSANQCAVPAKDRVDCGYPHVTPKECNNRGCC FDSRIPGVPWCFKPLQEAECTF (SEQ ID NO: 24) | Trefoil factor | Anti-inflammatory Binds mucosa |
| Lunasin | SKWQHQQDSCRKQLQGVNLTPCEKHIMEKIQGRGDDD DD DDDD (SEQ ID NO: 32) | Soybean 2S albumin | Anti-inflammatory |
| MAM | MMMPANYSVIAENEMTYVNGGANFIDAIGAVT APIWTLDNVKTFNTNIVTLVGNTFLQSTINRTIVL FSGNTTWKEVGNIGKNLFGTNVKGNPIEKNNFGDYAMN ALGIAAAVYNLGVAPTKNTVKETEVKFTV (SEQ ID NO: 33) | Faecalibacterium prausnitzii | Anti-inflammatory |

We have identified specific combinations of linker sequences and culture conditions that lead to optimal curli fiber formation for each of the different fusion domains is provided in Table 3 below.

| CsgA-peptide construct | Optimal linker domain (SEQ ID NO: 40) | Optimal [IPTG] (mM) | Temperature (C.) | Duration (h) |
|---|---|---|---|---|
| CsgA-TFF1 | 48 AA (GGGS)$_n$ | 0.3 | 37 | 24 |
| CsgA-TFF2 | 24 AA (GGGS)$_n$ | 0.3 | 37 | 24 |
| CsgA-TFF3 | 24 AA (GGGS)$_n$ | 0.3 | 37 | 24 |
| CsgA-lunasin | 36 AA (GGGS)$_n$ | 0.3 | 37 | 24 |
| CsgA-MAM | 36 AA (GGGS)$_n$ | 0.3 | 37 | 24 |
| CsgA-T18 | 48 AA (GGGS)$_n$ | 0.3 | 25 | 48 |
| CsgA-CP15 | 48 AA (GGGS)$_n$ | 0.3 | 25 | 48 |
| CsgA-P8 | 48 AA (GGGS)$_n$ | 0.3 | 25 | 48 | expression of the CsgA-linker-functional polypeptide to the system. Such a system is described in *Lab Chip,* 2012,12, 2165-2174, hereby incorporated by reference in its entirety.

Exemplary polypeptide or protein sequences having affinity with tissues or cells associate with the GI tract can be determined from monitoring or determining spatiotemporal distribution in mouse models. According to this aspect, engineered bacteria strains, such as engineered Nissle strains, are administered orally, such as a single dose, to the healthy mouse gut followed by a period of normal feeding. Residence time of the engineered strains will be measured by CFU counting from fecal samples collected daily. Spatial localization within the gut will be monitored by harvesting the gut tissue, sectioning, and tracking the presence of engineered strains by CFU counts from homogenized tissues and immune staining of histological tissue slices.

Several linkers were tested in a library of polypeptide domains that are known to bind to gut epithelia in a localized manner. Known as trefoil factors (TFFs), this polypeptide family consists of 3 identified peptides (TFF1, TFF2, and TFF3), that are secreted by the gastrointestinal mucosa and differentially bind to different areas of the gastrointestinal tract. All trefoil factors have in common a trefoil domain, which consists of three conserved disulfide bonds. The sequence for each TFF construct engineered into a CsgA-linker is shown in Table 2 above.

Figure 4:
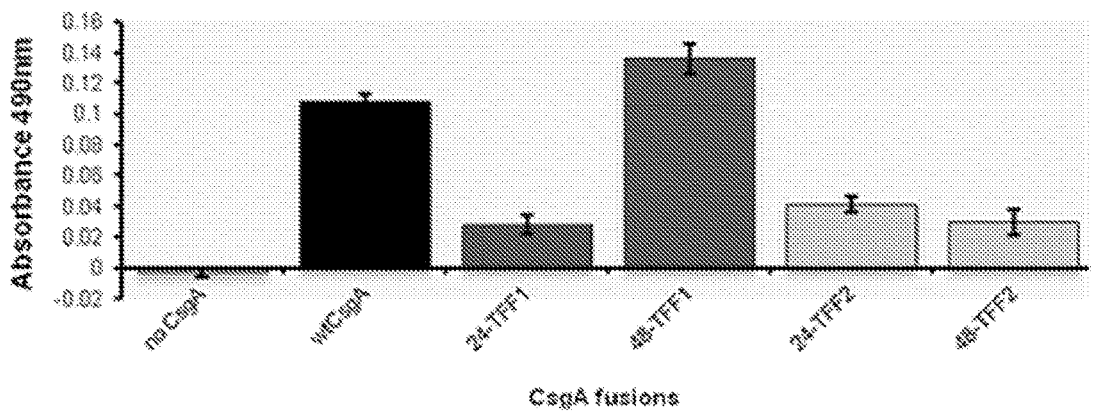
FIG. 4 is a graph depicting expression of curli nanofibers fused with trefoil factor proteins determined by a CR absorbance assay for various CsgA-TFF constructs with various length flexible linker domains. The data was obtained from a PHL628 strain.

TFF1 contains a single trefoil domain of 60 amino acids. TFF2 contains two homologous trefoil domains, resulting in a total of 6 disulfide bonds, and is over 100 amino acids in length. Various constructs were made containing CsgA fused to the TFF2 via the flexible linkers identified in the preceding experiments. For the single trefoil domain construct (TFF1), longer flexible linker domains resulted in a marked improvement in expression levels as measured by a quantitative Congo Red binding assay (FIG. 4).

TFF1 showed nearly a 5-fold increase when the flexible linker length was increased from 24 to 48 residues. In contrast, TFF2 showed no improvement as a function of linker length, which may be due to the complexity of the protein (6 disulfides) or larger length (>100 amino acids).

Various short peptides (7-12 amino acids) were tested, using the F48 linker as shown in Table 4.

expresses curli nanofibers. The Nissle strain was isolated during WWI from the fecal samples of a soldier who was resistant to infectious enteropathogenic diarrhea. Further studies have shown the Nissle strain to be a profound probiotic, with the ability to protect against gastroinvasive bacteria and to ameliorate other gastrointestinal disorders such as ulcerative colitis, irritable bowel syndrome, and Crohn's disease. Accordingly, aspects of the present disclosure are directed to attaching Nissle E. coli to gut tissue.

Figure 8A:
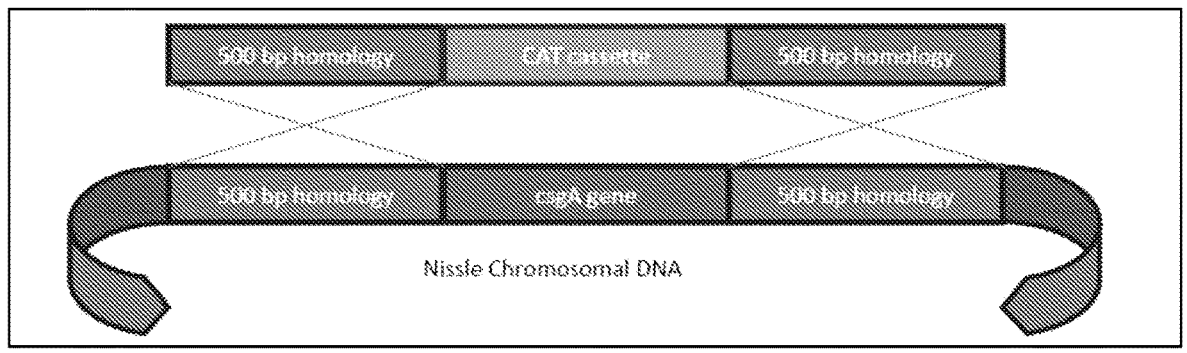
Figure 8B:
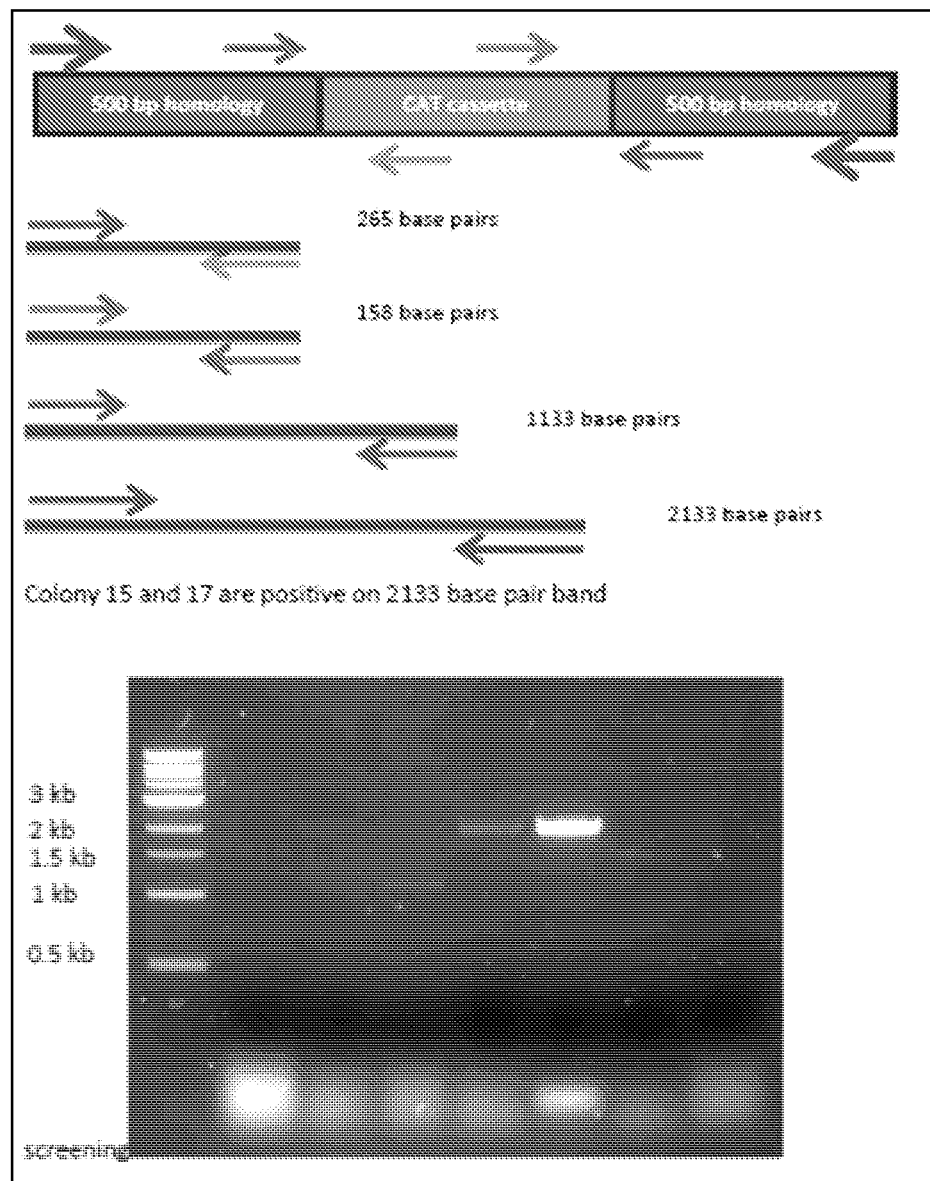

The endogenous CsgA gene was removed from the Nissle strain using the Lambda Red genomic deletion technique, resulting in an engineered strain of Nissle (Nissle mutant, PBP17) with a precise csgA deletion. FIG. 8A-8D shows construction of a CsgA deletion mutant of Nissle 1917. FIG. 8A shows a lambda red recombination strategy for the deletion of the csgA gene in Nissle. FIG. 8B shows PCR validation of the chloramphenicol cassette insertion at the csgA locus identifies two positive clones (black arrows). FIG. 8C shows two clones verified for the presence of the 265, 158, and 113 bp amplicons. FIG. 8D shows sequencing verification of the regions flanking the csgA gene indicates successful CAT cassette integration (highlighted in yellow). To test the adhesion functionality of the various constructs expressed in PBP17, an in vitro binding study to Caco-2

TABLE 4

BIND Variants for Small Peptide Gut Epithelial Tissues.

| Plasmid Name | Peptide domain Sequence | Gut Localization | Ref. |
|---|---|---|---|
| pBbE1a-CsgA-F48-T18 | LTHPQDSPPASA (SEQ ID NO: 25) | Injured epithelial cells | Costantini TW, et al.[1] |
| pBbE1a-CsgA-F48-CP15 | VHLGYAT (SEQ ID NO: 26) | Colon cancer | Zhang Y, et al.[2] |
| pBbE1a-CsgA-F48-P8 | LETTCASLCYPS (SEQ ID NO: 27) | M cells, FAE | Higgins L et al.[3] |
| pBbE1a-CsgA-F48-A1 | VRPMPLQ (SEQ ID NO: 28) | Colon cancer | Hsiung PL et al.[4] |

Figure 5:
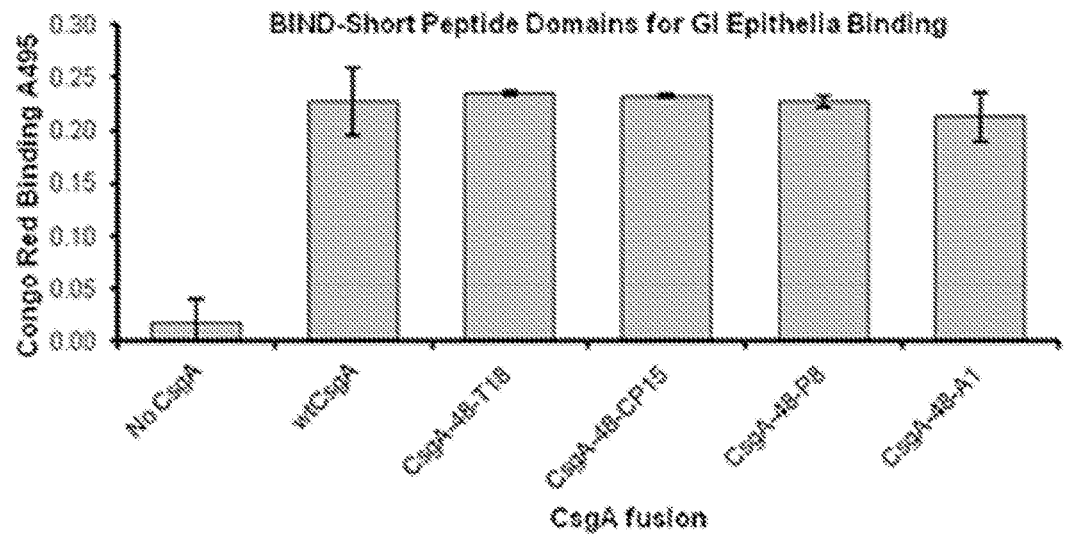
FIG. 5 is a graph depicting expression of curli nanofibers fused with gut binding short peptide domains using a Congo red binding assay of wild type CsgA compared to CsgA fused to four different peptides that have been shown to bind to specific gut tissues. The data was obtained from a PHL628 strain.

These peptides have been identified through phage-display techniques for binding to the intestinal mucosa. As shown in FIG. 5, all of these short peptide constructs demonstrated export and curli-self-assembly levels comparable to that of the wild type CsgA.

Figure 6:
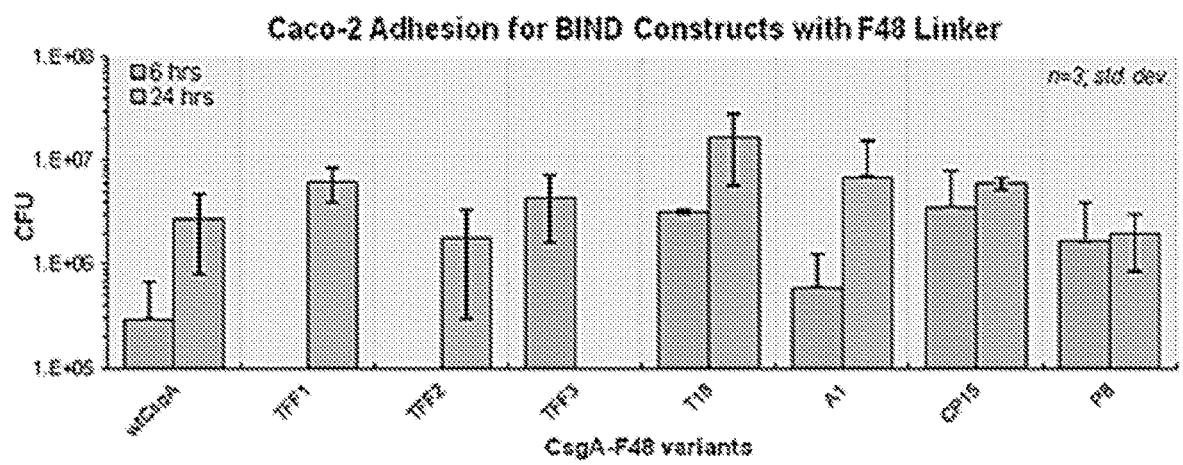
FIG. 6 is a graph depicting adhesion of LSR10 cells harboring gut-binding domains to Caco-2 cells where constructs with the F48 linker and containing trefoil domains TTF1, TTF2, and TTF3, or small peptides T18, A1, CP15 and P8 were tested for in vitro binding to Caco-2 monolayers. Bound cells were recovered and quantified by CFU analysis.
Figure 7:
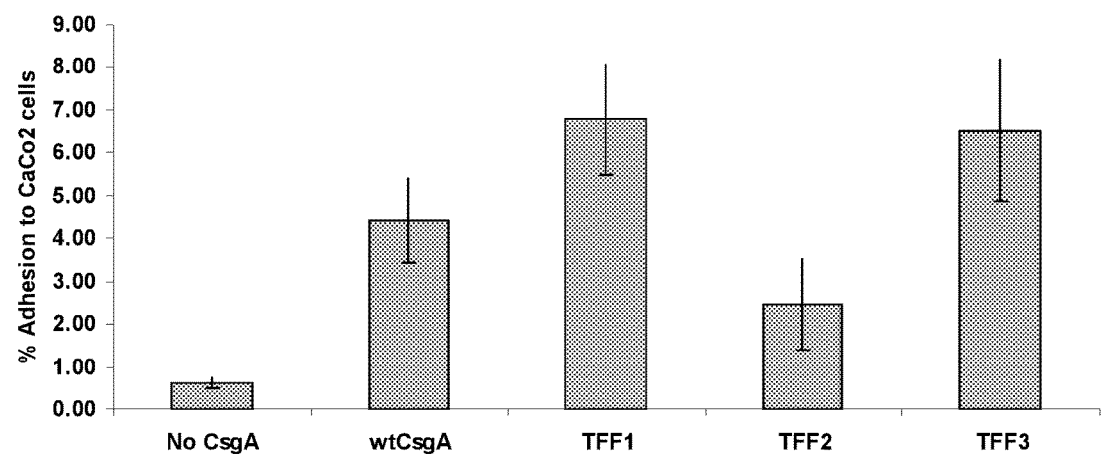
FIG. 7 is a graph depicting adhesion of PHL628 cells producing engineered curli fibers to Caco-2 cell monolayers. When no curli is produced, adhesion decreases significantly, suggesting that the wild type curli fibers may play a role in adhesion to epithelial surfaces. TTF1 and TTF3 increase adhesion to the epithelial surface.

To test if these various gut-binding domains (TFFs and the short peptides) retained their tissue homing functions when displayed on curli nanofibers, standard in vitro assays for bacterial binding to Caco-2 cell monolayers was performed. Caco-2 cell lines are phenotypically similar to the enteric columnar epithelial cells that line the human small intestine. These cell lines are widely used in research laboratories as model in vitro systems. Various CsgA constructs, all containing the F48 linker domain, were expressed in the E. coli LSR10 strain. This strain of E. coli is a laboratory K-12 strain which produces no other extracellular organelles (cellulose, flagella, pili, etc.), thus allowing for clear discernment of function. FIG. 6 shows adhesion of LSR10 cells expressing CsgA constructs with gut-binding domains to Caco-2 cells. Various CsgA constructs, all containing the F48 linker domain, were expressed in the E. coli PHL628 strain. FIG. 7 shows adhesion of PHL628 cells expressing CsgA constructs with gut-binding domains to Caco-2 cells.

Figure 9:
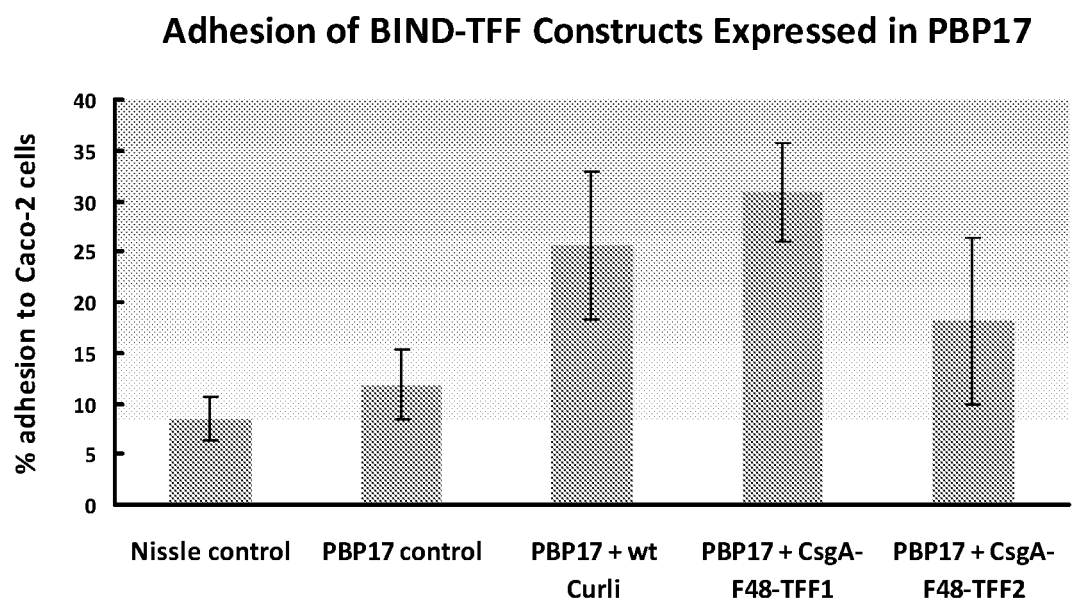
FIG. 9 is a graph depicting adhesion of Nissle PBP17 harboring gut-binding TFFs to Caco-2 cells. Constructs with the F48 linker and containing trefoil domains (TFF1, TFF2, and TFF3) were expressed in a Nissle ΔcsgA mutant (PBP17) and tested for in vitro binding to Caco-2 monolayers. Bound cells were recovered and quantified by CFU analysis and the data is presented as the percent bound compared to the initial inoculum.

The expression and binding of the constructs were further tested in a probiotic strain of E. coli, Nissle 1917, which cells was performed as described above. Constructs with the F48 linker and containing trefoil domains (TFF1, TFF2, and TFF3) were expressed in a Nissle ΔcsgA mutant (PBP17) and tested for in vitro binding to Caco-2 monolayers. Bound cells were recovered and quantified by CFU analysis and the data is presented in FIG. 9 as the % of total inoculated bacterial cells that remained adhered to the Caco-2 monolayer.

Exemplary structures include (SEQ ID NO: 41)
CsgA-(GGGS)$_n$-TTF1,
wherein n is 3, 6 or 9.

(SEQ ID NO: 41)
CsgA-(GGGS)$_n$-TTF2,
wherein n is 3, 6 or 9.

(SEQ ID NO: 41)
CsgA-(GGGS)$_n$-TTF3,
wherein n is 3, 6 or 9.

(SEQ ID NO: 41)
CsgA-(GGGS)$_n$-T18,
wherein n is 3, 6 or 9.

-continued

CsgA-(GGGS)$_n$-CP15, (SEQ ID NO: 41)
wherein n is 3, 6 or 9.

CsgA-(GGGS)$_n$-P8, (SEQ ID NO: 41)
wherein n is 3, 6 or 9.

EXAMPLE VI

Treating Chronic Inflammatory Diseases of the Gut

Aspects of the present disclosure are directed to methods of treating chronic inflammatory diseases of the gut, such as inflammatory bowel disease and Crohn's disease by administering to an individual in need thereof a certain engineered bacterial strain or strains as described herein. According to one aspect, the bacterial strain expresses a CsgA-linker-anti-inflammatory polypeptide construct.

The bacterial strain expresses the CsgA-linker-anti-inflammatory polypeptide construct and the anti-inflammatory polypeptide treats the chronic inflammatory disease of the gut.

According to one aspect, the bacterial strain expresses a CsgA-linker-first member of a binding pair polypeptide construct. The second member of the binding pair attached to an anti-inflammatory compound is then administered. The first member of the binding pair and the second member of the binding pair bind thereby localizing the anti-inflammatory compound, for example, to the gut, for the treatment of chronic inflammatory diseases of the gastrointestinal tract.

According to one aspect, the bacterial strain is a non-pathogenic bacterial strain, such as the Nissle strain or any other non-pathogenic strain known to those of skill in the art such as MG1655, K12-derived strains, and the like.

The anti-inflammatory compound can be a protein sequence capable of abrogating inflammatory processes in the gut. Exemplary protein sequences include the trefoil factor family of peptides (TFFs) because they are endogenous signaling molecules in the mammalian gut, have demonstrated efficacy in treating IBD and Crohn's in the clinic, and are under development in their soluble form as biologics for these indications.

According to one aspect, the anti-inflammatory compound, protein or polypeptide may exert its effects while still attached to the engineered curli fibers. According to one aspect, the anti-inflammatory compound, protein or polypeptide may exert its effects as a soluble protein or compound after cleavage from the curli fibers by a protease. Several proteases in the MMP family (MMP2, MMP9 and the like) are upregulated during inflammation and may be used to cleave the anti-inflammatory compound, protein or polypeptide from the linker domain.

According to one aspect, methods are provided to deliver bioactive proteins and peptides locally to the inflamed gut. According to one aspect, methods are provided to deliver bioactive proteins and peptides locally to the inflamed gut in response to specific inflammatory cues.

Anti-inflammatory compound, protein or polypeptide may be identified by the exemplary methods described below for TTF domains. Caco-2 intestinal epithelial cells grown in 2D culture are treated with purified curli fibers displaying TFF domains. Biomarkers indicative of TFF bioactivity are monitored such as cell migration speed as TFFs are known to promote cell migration. The migration speeds for assembled curli fibers composed of either wt-CsgA (neg. ctrl), CsgA-TFF, or soluble TFF (positive ctrl) are compared. Migration speeds are measured using a wound healing assay on confluent monolayers. If TFF is active, it will increase migration speeds, comparable to the soluble TFFs.

According to another method, levels of COX-2 expression in the three cell populations are compared by Western blot. Expression above the negative control confirms the bioactivity of the curli-bound TFFs.

According to another method, a Gut-on-a-Chip system is used to measure the bioactivity of the curli-bound TFFs using a more physiologically-relevant model system. Chronic inflammation is simulated by adding inflammatory agents (e.g. LPS) to a chip containing an epithelial layer, endothelial layer, and circulating immune cells. See Kim et al., LabChip 12, 2165 (2012) and Kim et al., Integrative biology: quantitative Biosciences from nano to Macro 5, 1130 (2013). The expression of key inflammatory markers (NF-κB, IL-1β, IL-8, COX-2, EGFR activation, etc.) is then monitored in response to treatment with curli-bound TFFs.

According to another method, established mouse models of intestinal inflammation (DSS, IL-10 knockout, etc.) are used to test the anti-inflammatory effects of the curli-bound TFFs. Abrogated inflammatory responses are measured qualitatively by histology and quantitatively with qPCR of key inflammatory cytokines.

EXAMPLE VII

Treating Cancers of the Gut

Aspects of the present disclosure are directed to methods of treating cancer such as cancer of the GI tract by administering to an individual in need thereof a certain engineered bacterial strain or strains as described herein. According to one aspect, the bacterial strain expresses a CsgA-linker-cancer treating polypeptide construct. Certain cancer treating polypeptides include those having known activity against cancers including growth inhibiting factors such as bevacizumab, cetuximab, panitumumab and the like.

The bacterial strain expresses the CsgA-linker-cancer treating polypeptide construct and the cancer treating polypeptide treats the cancer tissue or cancer cells. According to one aspect, the bacterial strain expresses a CsgA-linker-first member of a binding pair polypeptide construct. The bacterial strain expresses the CsgA-linker-first member of a binding pair polypeptide construct. The second member of the binding pair attached to a cancer treating compound is then administered. The first member of the binding pair and the second member of the binding pair bind thereby localizing the cancer treating compound, for example, to the gut, for the treatment of cancer, such as cancers of the gastrointestinal tract.

Useful bacterial strains include non-pathogenic E. coli, such as the E. coli Nissle 1917 (EcN), MG1655, K12-derived strains and the like.

According to one aspect, the cancer treating protein or polypeptide may exert its effects while still attached to the engineered curli fibers. According to one aspect, the cancer treating protein or polypeptide domain may exert its effects as a soluble protein after cleavage from the curli fibers by a protease. Several proteases in the MMP family are upregulated during inflammation and may be used to cleave the cancer treating polypeptide from the linker domain.

Methods described above can be used to confirm both in vitro and in vivo activity of this embodiment of the disclosure.

EXAMPLE VIII

Diagnostic Methods

Aspects of the present disclosure are directed to methods of delivering a diagnostic agent, such as a marker, to a site within a mammal by administering to the mammal a certain engineered bacterial strain or strains as described herein. According to one aspect, the bacterial strain expresses a CsgA-linker-diagnostic polypeptide construct.

The bacterial strain expresses the CsgA-linker-diagnostic polypeptide construct and the diagnostic polypeptide is detected. According to one aspect, the bacterial strain expresses a CsgA-linker-first member of a binding pair polypeptide construct. The bacterial strains express the CsgA-linker-first member of a binding pair polypeptide construct. The second member of the binding pair attached to a diagnostic compound is then administered. The diagnostic compound may include an imaging agent or dye. The first member of the binding pair and the second member of the binding pair bind thereby localizing the diagnostic compound to the location of interest, such as the gut.

Useful bacterial strains include non-pathogenic E. coli, such as the Nissle strain, MG1655, K12-derived strains and the like.

According to one aspect, the diagnostic polypeptide or diagnostic compound may be still attached to the engineered curli fibers. According to one aspect, the diagnostic polypeptide or the diagnostic compound may be cleaved from the curli fibers by a protease. Several proteases in the MMP family are upregulated during inflammation and may be used to cleave the diagnostic polypeptide or diagnostic compound from the linker domain.

According to one aspect, the diagnostic polypeptide or diagnostic compound may be released from the curli fibers using a protease-cleavable linker. According to this aspect, a recombinant construct of CsgA-linker-diagnostic polypeptide is made where the linker domain includes an amino acid sequence that is recognized and cleaved by a protease enzyme. Such amino acid sequences and associated protease enzymes are known to those of skill in the art and include MMPs, CD2830 and the like. The linker may be selected such that it is susceptible to cleavage by enzymes that are produced locally at sites of inflammation (MMP2, MMP9, etc.). Methods described above can be used to confirm both in vitro and in vivo activity of this embodiment of the disclosure.

EXAMPLE IX

Treatment of Gut Borne Pathogens

Aspects of the present disclosure are directed to methods of treating gut borne pathogens by administering to an individual in need thereof a certain engineered bacterial strain or strains as described herein. According to one aspect, the bacterial strain expresses a CsgA-linker-antimicrobial polypeptide construct. Certain antimicrobial polypeptides or proteins include any polypeptide or protein sequence having antimicrobial activity. Antimicrobial peptides for use in a therapeutic context are known to those of skill in the art. See Cotter, P. D., Ross, R. P. & Hill, C. Bacteriocins—a viable alternative to antibiotics? Nat Rev Micro 11, 95-105 (2012); Hing, T. C. et al. The antimicrobial peptide cathelicidin modulates Clostridium difficile-associated colitis and toxin A-mediated enteritis in mice. Gut 62, 1295-1305 (2013); Nulling, S., Frasch, T., Schaller, M., Stange, E. F. & Zabel, L. T. Synergistic Effects of Antimicrobial Peptides and Antibiotics against Clostridium difficile. Antimicrobial Agents and Chemotherapy 58, 5719-5725 (2014); Rea, M. C. et al. Thuricin CD, a posttranslationally modified bacteriocin with a narrow spectrum of activity against Clostridium difficile. Proc Natl Acad Sci USA 107, 9352-9357 (2010); Petrof, E. Probiotics and Gastrointestinal Disease: Clinical Evidence and Basic Science. AIAAMC 8, 260-269 (2009). Kang, J. K. et al. The Insect Peptide Coprisin Prevents Clostridium difficile-Mediated Acute Inflammation and Mucosal Damage through Selective Antimicrobial Activity. Antimicrobial Agents and Chemotherapy 55, 4850-4857 (2011); and Ostaff, M. J., Stange, E. F. & Wehkamp, J. Antimicrobial peptides and gut microbiota in homeostasis and pathology. EMBO Mol Med 5, 1465-1483 (2013).

According to one aspect, gut borne pathogens include Clostridium difficile, Salmonella typhimurium, Enteropathogenic E. coli, Helicobacter pylori and the like.

The bacterial strain expresses the CsgA-linker-antimicrobial polypeptide construct and the antimicrobial polypeptide treats the gut borne pathogens in a manner to reduce or eliminate the gut borne pathogens. According to one aspect, the bacterial strain expresses a CsgA-linker-tissue or cell binding polypeptide construct. The bacterial strain expresses the CsgA-linker-tissue or cell binding polypeptide construct and the bacterial strain treats the gut borne pathogens in a manner to reduce or eliminate the gut borne pathogens. According to one aspect, the bacterial strain expresses a CsgA-linker-first member of a binding pair polypeptide construct. The bacterial strains express the CsgA-linker-first member of a binding pair polypeptide construct. The second member of the binding pair attached to an antimicrobial compound is then administered. The first member of the binding pair and the second member of the binding pair bind thereby localizing the antimicrobial compound to the gut for the treatment of the gut borne pathogens in a manner to reduce or eliminate the gut borne pathogens.

Useful bacterial strains include non-pathogenic E. coli, such as the E. coli Nissle 1917 (EcN), MG1655, K12-derived strains and the like.

According to one aspect, the antimicrobial protein or polypeptide may exert its effects while still attached to the engineered curli fibers. According to one aspect, the antimicrobial protein or polypeptide may exert its effects as a soluble protein after cleavage from the curli fibers by a protease. Several proteases in the MMP family are upregulated during inflammation and may be used to cleave the bioactive domain from the linker domain.

According to one aspect, the antimicrobial proteins or peptides may be released from the curli fibers using a protease-cleavable linker According to this aspect, a recombinant construct of CsgA-linker-antimicrobial is made where the linker domain includes an amino acid sequence that is recognized and cleaved by a protease enzyme. Such amino acid sequences and associated protease enzymes are known to those of skill in the art. The linker may be selected such that it is susceptible to cleavage by enzymes that are produced locally at sites of inflammation (MMP2, MMP9, etc.). According to one aspect, antimicrobial proteins are fused to the curli fibers via a linker that is susceptible to cleavage by the proteolytic virulence factor CD2830. According to one aspect, antimicrobial proteins are released inside the gut only in the presence of *C. difficile* virulence factors. The antimicrobial protein is delivered locally to kill the invading pathogen.

Methods described above can be used to confirm both in vitro and in vivo activity of this embodiment of the disclosure.

There are several examples of antimicrobial proteins with demonstrated activity against *C. difficile*, including thurcin CD, lantibiotics like nisin and actagardine, cathelicidins and LL-37. One exemplary antimicrobial protein is coprisin, a peptide that was originally isolated from *Copris tripartitus* (a Korean dung beetle) that has recently shown promise as a treatment for *C. difficile* infections. Coprisin has a high potency against *C. difficile* (MIC of 1.5 µg/mL compared to 3.0 µg/mL for vancomycin) and a lack of activity against common gut commensals like *Lactobacillus* and *Bifidobacterium*. The full coprisin peptide is 43 amino acids, but a 9 amino acid truncated analog (LLCIALRKK) (SEQ ID NO:29) exhibits higher antibiotic activity. The coprisin-derived sequence is fused to CsgA through a linker that is susceptible to cleavage in the presence of a protease virulence factor secreted by *C. difficile* during infection. See Hensbergen, P. J. et al. A novel secreted metalloprotease (CD2830) from *Clostridium difficile* cleaves specific proline sequences in LPXTG (SEQ ID NO:30) cell surface proteins. Molecular & Cellular Proteomics 13, 1231-1244 (2014). CD2830 is a metalloprotease that is actively secreted by *C. difficile* into the extracellular space and is thought to play a role in pathogen motility by cleaving adhesions that bind to the epithelial cell surface. Importantly, CD2830 is known to exhibit specificity for cleavage of proline-rich sequences, especially Pro-Pro and sortase-like LPXTG (SEQ ID NO:30) sequences.

Figure 10:
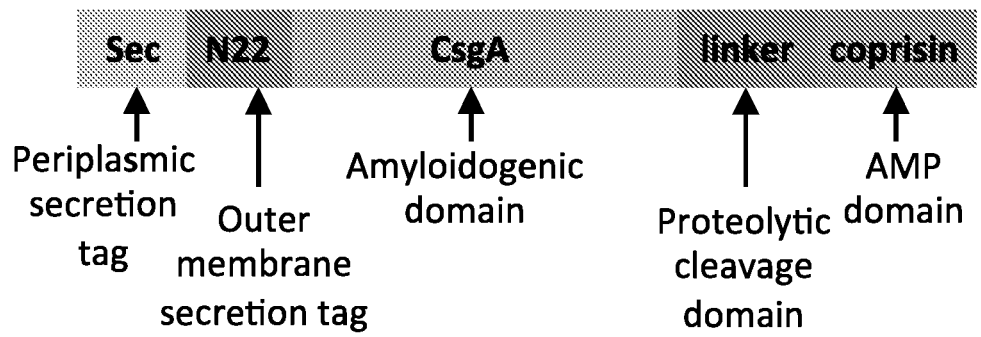
FIG. 10 depicts a diagram of CsgA-linker-AMP constructs to be synthesized and screened. Sec is a periplasmic secretion tag that is cleaved after transport. N22 is the outer membrane secretion tag. CsgA is the amyloidogenic region of the protein. Linkers will have the general sequence $(GGS)_n$XXXX, with n=3, 4, or 5 and XXXX=PPP, PPIP, or PPVP (SEQ ID NO:3). The total panel size will be 9 members, with fused domains ranging from 22-28 amino acids.

A panel of CsgA-linker-coprisin variants is constructed using a combination of direct synthesis of peptide inserts (via Integrated DNA Technologies) and overlap extension PCR. The gene panel will vary in the length and sequence of the linker region as shown in FIG. 10 in order to identify an optimal sequence for export and cleavage. Proline-rich regions were selected based on the fastest cleavage rates when subjected to CD2830, as reported by Hensbergen, et al. FIG. 10 is a diagram of CsgA-linker-AMP constructs for synthesis and screening. Sec is a periplasmic secretion tag that is cleaved after transport. N22 is the outer membrane secretion tag. CsgA is the amyloidogenic region of the protein. Linkers have the general sequence (GGS)$_n$XXXX, with n=3, 4, or 5 and XXXX=PPP, PPIP, or PPVP (SEQ ID NO:31). The total panel size is 9 members, with fused domains ranging from 22-28 amino acids.

These genes are incorporated into the appropriate plasmids using previously reported protocols. The plasmids harbor ampicillin resistance genes for antibiotic selection and the genes encoding for the CsgA fusion proteins are placed under the control of an IPTG inducible promoter.

Genetic constructs are made and introduced into EcN and the ability of EcN to synthesize, secrete, and assemble curli fibers displaying the linker-AMP domains is tested. Plasmids encoding for the CsgA-linker-AMP constructs are transformed into a mutant of EcN in which the genomic copy of the csgA gene has been deleted and replaced with an antibiotic selection marker (EcN-ΔcsgA). This mutant is unable to produce curli fibers of its own, so any curli-related signals obtained after plasmid transformation arise from the engineered curli constructs. Congo Red staining is used to rapidly screen for curli production in engineered *E. coli* variants. In addition, curli production is assayed using a whole-cell ELISA assay wherein induced EcN-ΔcsgA transformants are filtered onto a membrane and probed directly with anti-CsgA antibodies. Transformants are characterized using SEM to confirm that the morphology of the modified curli fibers is qualitatively similar to the wild-type fibers. In order to confirm that the linker-AMP domains remain intact and have not been degraded during the secretion and assembly process, an established purification protocol is used to obtain pure curli fibers, which are disassembled and subjected to MALDI-mass spectrometry analysis. Comparison between growth rates of the various tranformants and EcN-ΔcsgA in minimal media is used as a proxy for fitness.

According to one aspect, the bioactive peptide is cleaved and released from the curli fibers in response to a protease. Suitable proteases can be identified using the following method which is exemplified by protease CD2830. The CD2830 protease is actively secreted by *C. difficile*, and is purported to act as a virulence factor by cleaving host protein-binding adhesions produced by the pathogen, thereby promoting motile phenotypes. CD2830 cleaves proline-rich sequences. Accordingly, linker domains include one or more prolines.

CD2830 is expressed recombinantly in *E. coli* and purified. A 96-well filter plate assay is used to subject biofilms to various conditions and to monitor the capture or release of soluble entities from the biofilm. A panel of engineered EcN variants are grown and induced in suspension culture, then immobilized with their associated curli fibers on the filter plate. The biofilms are washed to remove all soluble or weakly bound biomolecules. The biofilms are treated with the recombinant CD2830 at various concentrations. Release of the AMPs is monitored at a range of time points to determine the kinetic parameters of the cleavage from assembled curl fibers. AMP release is monitored by LC-MS analysis of the collected fractions after protease treatment. Similar release studies is performed with a live *C. difficile* strain (ATCC 43255) by exposure of the filtered biofilms to the pathogen inside an anaerobic chamber.

Antimicrobial activity of antimicrobial proteins, such as coprisin, by two different assays of the modified curli fibers—one that mimics a conventional minimum inhibitory concentration (MIC) assay, and another that monitors the cytotoxicity of *C. difficile* cells after culture in the presence of modified curli fibers. In the first assay, EcN variants that are selected for their ability to release active AMP in response to recombinant CD2830 are induced in YESCA media to form modified curli fibers. The induced cell cultures are grown to an $OD_{600}$=1, then heat-treated to kill the EcN cells before being transferred to an anaerobic chamber. *C. difficile* cultures are prepared by growing them overnight under anaerobic conditions to stationary phase. They are then be incubated with the AMP-displaying curli fibers at various concentrations for a range of times. Finally, viable *C. difficile* cells are counted by plating serial dilutions on agar plates with the appropriate growth medium and counting colony forming units (CFUs). In the second assay, the ability of engineered EcN variants to protect human epithelial cell layers from invasion by vegetative *C. difficile* is tested. Using a published protocol, the colorectal cancer-derived Caco-2 cell line (ATCC HTB37) is grown to confluency in 96-well plates. See Wagner, R. D., Johnson, S. J. & Cerniglia, C. E. In Vitro Model of Colonization Resistance by the Enteric Microbiota: Effects of Antimicrobial Agents Used in Food-Producing Animals. Antimicrobial Agents and Chemotherapy 52, 1230-1237 (2008).; Banerjee, P., Merkel, G. J. & Bhunia, A. K. *Lactobacillus delbrueckii* ssp. *bulgaricus* B-30892 can inhibit cytotoxic effects and adhesion of pathogenic *Clostridium difficile* to Caco-2 cells.

Gut Pathog 1, 8 (2009). The cell lines are then incubated with the engineered EcN variants for 3 hours before being washed with cell culture media to remove non-adhered cells. The cell monolayers are exposed to vegetative *C. difficile* cells under aerobic conditions and co-incubated for 3 hours. Cytotoxicity is monitored using a LIVE/DEAD fluorescent staining assay coupled with image-based detection of cell counts.

The altered CsgA genes are incorporated into the genome of EcN. A mutant of EcN is generated wherein the csgA gene has been replaced with an antibiotic selection marker by using a lambda Red recombineering technique wherein a double stranded DNA insert containing a desired selection marker flanked by homology domains specific for the csgA locus is introduced into the bacterial cells along with the lambda Red recombination factors. See Datsenko, K. A. & Wanner, B. L. One-step inactivation of chromosomal genes in *Escherichia coli* K-12 using PCR products. *Proc Natl Acad Sci USA* 97, 6640-6645 (2000). The genome edited clones are selected by plating on antibiotic selective plates and the presence of the correct insertion is confirmed by PCR and sequencing. The resulting strain, referred to as EcN-ΔcsgA, does not produce curli fibers. A similar lambda Red recombineering strategy is used to replace the csgA gene in wild-type EcN with genes encoding for CsgA-linker-AMP variants. The genetic insertion cassettes contain both the chimeric sequences and an antibiotic resistance marker for the selection of successfully edited clones. The resistance gene is flanked by flippase recognition target (FRT) domains that enable self-resection if treated by mild heat. Such a method provides "scarless" insertion of csgA variants.

Successfully edited clones are subjected to a range of characterization protocols to ensure that they produce curli fibers. Whole cell ELISA is used to confirm the presence of assembled CsgA in the fibers. SEM is used to confirm that the gross morphology of the engineered fibers resembles that of wild-type curli fibers. MALDI-MS analysis of purified curli fibers is used to confirm that the linker and AMP domains are not degraded during the secretion and assembly process. Finally, growth rates in suspension culture are monitored for wild-type EcN, EcN-ΔcsgA, and each of the CsgA-linker-AMP constructs.

The viability of the EcN genomic mutants in the healthy mouse gut is tested. The engineered EcN mutants survive and transiently colonize the mouse gut without harming the host. Genomically altered EcN mutants are fed to healthy mice at CFU values of ~108. The inoculation occurs once, and the mice are fed a normal diet for 10 days. The residence time of the engineered EcN variants in the mouse gut is monitored by collecting fecal samples daily and counting viable colonies on Macconkey agar plates with the appropriate antibiotic selection. Mice are observed and their body weight measured daily in order to confirm that there are no symptoms of bacterial infection. At the experimental endpoint, the mice are sacrificed and their organs harvested in order to determine the spatial distribution of EcN cells. The GI tract is sectioned into upper, lower, and middle sections and homogenized before counting CFUs by serial dilution on selective plates. A similar protocol is applied to the liver and spleen to check for invasive phenotypes.

The therapeutic effects of the engineered EcN variants on gut inflammation following *C. difficile* infection are monitored using the mouse model of antibiotic-induced *C. difficile*-associated disease (CDAD) developed by Kang, et al., which more closely resembles human disease responses compared to other available models. Mice in similar test groups are housed together and pre-treated with water containing a cocktail of antibiotics (gentamicin, metronidaxole vancmycin, and colistin at appropriate dosages). Control mice receive a single dose of clindamycin (10 mg/kg) intraperitoneally, whereas experimental mice receive clindamycin intraperitoneally plus $10^8$ CFU of the engineered EcN variant via oral gavage. One day later, all mice are infected by oral gavage with 0.5 ml of a suspension of *C. difficile* strain VPI 10463 ($5\times10^8$ CFU/ml). Control mice are further given drinking water alone, and experimental mice are also further administered the EcN variants orally for 6 days and monitored for weight loss and survival. Fecal samples are collected daily and tissues are collected on day 10, and the localization of the EcN is measure by CFU counting and immunohistochemistry.

EXAMPLE X

Selective Capture of Harmful Agents, Toxins or Metabolites

Aspects of the present disclosure are directed to methods of capturing capture targets such as harmful agents, toxins or metabolites by administering to an individual in need thereof a certain engineered bacterial strain or strains as described herein. According to one aspect, the bacterial strain expresses a CsgA-linker-capture agent polypeptide construct. Certain capture agents and associated capture targets include cholesterol and cholesterol-binding-peptides, phosphate and phosphate-binding-peptides, gliadin and gliadin-binding peptides and the like and those readily identified through literature search. Representative examples are shown in Table 5 below.

| Name | Sequence | Origin | Function |
| --- | --- | --- | --- |
| L4F peptide | DWFKAFYDKVAEKFKEAF (SEQ ID NO: 34) | Apolipoprotein E | Cholesterol binding |
| Alpha synuclein peptide | GGAVVTGVTAVA (SEQ ID NO: 35) | Alpha synuclein protein | Cholesterol binding |
| P61 | VRPMPLQ (SEQ ID NO: 36) | Phage Display | Gliadin binding |
| P64 | LTHPQDSPPASA (SEQ ID NO: 37) | Phage Display | Gliadin binding |
| GlnBP | LVVATDTAFVPFEFKQGDKYVGFDVDL WAAIAKELKLDYELKPMDFSGIIPALQT KNVDALAGITITDERKKAIDFSDGYYKS | glutamine-binding protein (GlnBP) | Gliadin binding |

-continued

| Name | Sequence | Origin | Function |
|---|---|---|---|
| | GLLVMVKANNNDVKSVKDLDGKVVAV<br>KSGTGSVDYAKANIKTKDLRQFPNIDNA<br>YMELGTNRADAVLHDTPNILYFIKTAGN<br>GQFKAVGDSLEAQYGIAFPKGSD<br>ELRDKVNGAL KTLRENGTYN<br>EIYKKWFGTE PK<br>(SEQ ID NO: 38) | | |

The bacterial strain expresses the CsgA-linker-capture agent polypeptide construct and the capture agent binds to the capture target. According to one aspect, the bacterial strain expresses a CsgA-linker-first member of a binding pair polypeptide construct. The second member of the binding pair attached to a capture agent is then administered. The first member of the binding pair and the second member of the binding pair bind thereby localizing the capture to the bacteria cell.

Useful bacterial strains include non-pathogenic E. coli, such as the Nissle strain, MG1655, K12-derived strains and the like.

According to one aspect, the capture agent protein or polypeptide may exert its effects while still attached to the engineered curli fibers. According to one aspect, the capture agent protein or polypeptide may exert its effects as a soluble protein after cleavage from the curli fibers by a protease. Several proteases in the MMP family are upregulated during inflammation or may be otherwise available in the gastrointestinal tract and may be used to cleave the bioactive domain from the linker domain.

According to one aspect, the capture agent proteins or peptides may be released from the curli fibers using a protease-cleavable linker According to this aspect, a recombinant construct of CsgA-linker-capture agent is made where the linker domain includes an amino acid sequence that is recognized and cleaved by a protease enzyme. Such amino acid sequences and associated protease enzymes are known to those of skill in the art. The linker may be selected such that it is susceptible to cleavage by enzymes that are produced locally at sites of inflammation (MMP2, MMP9, etc.). Methods described above can be used to confirm both in vitro and in vivo activity of this embodiment of the disclosure.

EXAMPLE XI

Engineered Bacteria as Live Diagnostics

Aspects of the present disclosure are directed to methods of delivering a diagnostic agent, such as a marker, to a site within a mammal by administering to the mammal a certain engineered bacterial strain or strains as described herein. According to one aspect, the bacterial strain expresses a CsgA-linker-diagnostic polypeptide construct.

The bacterial strain expresses the CsgA-linker-diagnostic polypeptide construct and the diagnostic polypeptide is detected. According to one aspect, the bacterial strain expresses a CsgA-linker-first member of a binding pair polypeptide construct. The bacterial strains express the CsgA-linker-first member of a binding pair polypeptide construct. The second member of the binding pair attached to a diagnostic compound is then administered. The first member of the binding pair and the second member of the binding pair bind thereby localizing the diagnostic compound to the location of interest, such as the gut.

Useful bacterial strains include non-pathogenic E. coli, such as the Nissle strain, MG1655, K12-derived strains and the like.

According to one aspect, the diagnostic polypeptide or diagnostic compound may be still attached to the engineered curli fibers. According to one aspect, the diagnostic polypeptide or the diagnostic compound may be cleaved from the curli fibers by a protease. Several proteases in the MMP family are upregulated during inflammation and may be used to cleave the diagnostic polypeptide or diagnostic compound from the linker domain.

According to one aspect, the diagnostic polypeptide or diagnostic compound may be released from the curli fibers using a protease-cleavable linker. According to this aspect, a recombinant construct of CsgA-linker-diagnostic polypeptide is made where the linker domain includes an amino acid sequence that is recognized and cleaved by a protease enzyme. Such amino acid sequences and associated protease enzymes are known to those of skill in the art. The linker may be selected such that it is susceptible to cleavage by enzymes that are produced locally at sites of inflammation (MMP2, MMP9, etc.). Methods described above can be used to confirm both in vitro and in vivo activity of this embodiment of the disclosure.

EXAMPLE XII

Additional Applications

Aspects of the present disclosure utilize the modified bacterial cells which express a fusion of a CsgA protein linked to a non-native functional polypeptide by a linker for biocatalysis. According to this aspect, methods are provided for the use of curli derived materials and biofilms as described herein as functionalizable surfaces for the immobilization of enzymes, such as enzymes used to perform chemical transformations in industrial applications (water purification, biofuel generation, etc.) and pharmaceutical applications (synthesis of drug intermediates). The CsgA-linker-immobilized enzyme includes the linkers described herein.

According to an additional aspect, methods are provided for metal removal or recovery. According to this aspect, methods are provided for the use of curli derived materials and biofilms as described herein as functionalizable surfaces for the immobilization of metals. The CsgA-linker-metal binding polypeptide or agent includes the linkers described herein. The metal binding polypeptide or agent may bind specific metals in ionic and metallic form.

According to additional aspects, methods are provided for bioremediation and for purification, such as by providing affinity purification matrices.

The curli system described herein is a biologically produced peptide-functionalized surface coating capable of being programmed to specifically immobilize another chemical or biological entity or to exhibit specific binding properties. The displayed peptide may possess intrinsic properties such as binding to other exogenously added functional components, such as inorganic nanoparticles (especially those with interesting opto-electronic properties or magneto-responsiveness), carbon-based nanostructures (i.e., graphene or nanotubes, which may confer conductivity), or environmental toxins (i.e., hormones or toxic metals). The engineered biofilms can also be used to display peptides that template the formation of inorganic or organic materials. Functionalizing the biofilm with peptides that specifically bind to different materials allows the surface coating of these materials in a genetically programmable manner. In addition, applications whereby the living biofilm is used to immobilize and present any arbitrary protein, as might be useful for applications in biocatalysis, biotemplating, or biosensing are specifically contemplated. According to one aspect, the synthesis and assembly of the material described herein is accomplished entirely by the bacterial cell, which acts as a factory for the production of programmed nanomaterials.

Additional specific applications include biologically-produced nanomaterials that have programmable optical, magnetoresistive or semiconductor properties from either the peptide/immobilized protein itself or by the induction of templated materials. By displaying catalytic peptides or enzymes on the curli biofilm, a system for high-efficiency immobilized biocatalysis in which various immobilization substrates can be used for the adhesion of the biofilm and which can be used in any bioreactor design is provided. The peptide/immobilized proteins can also encode for biologically active biomolecules that will allow the biofilm to act as a tissue scaffold or vaccine delivery material. Expression of peptide/immobilized proteins that bind to or enzymatically neutralize environmental toxins such as synthetic hormones, small molecules, or toxic metals is used as a biofilm-based technology for bioremediation. By expressing peptides that are able to specifically bind to precious metals such as gold, silver, platinum, and rhodium on the biofilms described herein, an active surface area for the profitable recovery of such precious materials is provided. The curli nanofibers can be engineered as conductive nanowires for numerous advanced materials applications by the display of peptides/proteins that are inherently conductive, or by the templating/anchoring of materials that are conductive. The use of bacteria to generate nanowires for energy storage based upon the expression on the curli biofilm of peptides capable of templating conductive or semiconductive materials, such as FePO4, is provided. Bacteria can be specifically engineered via the displayed peptide to bind strongly to specific substrates, such as steel, glass, or gold. Such material-specific binding can provides a biofilm-based biosensing apparatus. The curli nanofiber matrix can also be engineered to display peptides/proteins that interact with other molecules in order to enhance or alter the mechanical properties of another material. By engineering the curli to adhere to specific materials, the biofilm can act as a living coating capable of providing adaptive and regenerative benefits, such as biocatalysis on a wide variety of immobilization substrates, corrosion resistance to the material, enhanced biofilm coverage for microbial fuel cell applications, or act as an environmentally responsive organic(biofilm)-inorganic(substrate) material.

The invention claimed is:

1. A method of making a biofilm comprising
proliferating a bacteria cell including a nucleic acid sequence encoding a fusion of a CsgA protein linked to a non-native functional polypeptide by a linker to produce a population of bacteria cells expressing the fusion and forming a biofilm having the non-native functional polypeptide attached thereto,
wherein the linker is a polypeptide comprising 7 or more amino acids attached to either the C terminus or the N terminus of the CsgA protein;
wherein the linker comprises [GGGS]n, wherein n is an integer being 3, 6, or 12 as set forth in SEQ ID NOs:5-7;
comprises [P]n wherein n is an integer being 12 or 24 as set forth in SEQ ID NOs:8-9; or
comprises [EAAAK]n wherein n is an integer being 3 or 9 as set forth in SEQ ID NOs:10-11; and
wherein the non-native functional polypeptide is selected from the group consisting of Trefoil Factor 1 (TFF1), Trefoil Factor 2 (TFF2) and Trefoil Factor 3 (TFF3).

2. The method of claim 1, wherein the nucleic acid sequence was introduced into the bacteria cell by homologous recombination.

3. The method of claim 1, wherein the bacteria cell is *Escherichia coli*.

4. The method of claim 1, wherein the bacteria cell includes a genomic deletion of the CsgA gene.

5. The method of claim 1, wherein the non-native functional polypeptide is releasable.

6. The method of claim 1, wherein the bacteria cell is Nissle strain 1917 (EcN) and the linker is [GGGS]$_n$ wherein n is an integer being 3, 6, or 12 as set forth in SEQ ID NOs:5-7.

7. The method of claim 2, wherein the bacteria cell is *Escherichia coli*.

8. The method of claim 2, wherein the bacteria cell includes a genomic deletion of the CsgA gene.

9. The method of claim 2, wherein the non-native functional polypeptide is releasable.

10. The method of claim 2, wherein the bacteria cell is Nissle strain 1917 (EcN) and the linker is [GGGS]$_n$ wherein n is an integer being 3, 6, or 12 as set forth in SEQ ID NOs:5-7.

11. The method of claim 7, wherein the bacteria cell includes a genomic deletion of the CsgA gene.

12. The method of claim 7, wherein the non-native functional polypeptide is releasable.

13. The method of claim 7, wherein the bacteria cell is Nissle strain 1917 (EcN) and the linker is [GGGS]$_n$ wherein n is an integer being 3, 6, or 12 as set forth in SEQ ID NOs:5-7.

14. The method of claim 8, wherein the non-native functional polypeptide is releasable.

15. The method of claim 8, wherein the bacteria cell is Nissle strain 1917 (EcN) and the linker is [GGGS]$_n$ wherein n is an integer being 3, 6, or 12 as set forth in SEQ ID NOs:5-7.

16. The method of claim 9, wherein the bacteria cell is Nissle strain 1917 (EcN) and the linker is [GGGS]$_n$ wherein n is an integer being 3, 6, or 12 as set forth in SEQ ID NOs:5-7.

17. The method of claim 12, wherein the bacteria cell is Nissle strain 1917 (EcN) and the linker is [GGGS]$_n$ wherein n is an integer being 3, 6, or 12 as set forth in SEQ ID NOs:5-7.

18. The method of claim 11, wherein the non-native functional polypeptide is releasable.

19. The method of claim 18, wherein the bacteria cell is Nissle strain 1917 (EcN) and the linker is [GGGS]$_n$ wherein n is an integer being 3, 6, or 12 as set forth in SEQ ID NOs:5-7.

* * * * *

SEQUENCE LISTING

```
<160> NUMBER OF SEQ ID NOS: 40

<210> SEQ ID NO 1
<211> LENGTH: 151
<212> TYPE: PRT
<213> ORGANISM: Escherichia coli

<400> SEQUENCE: 1

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140
```

```
Asn Ala Thr Ala His Gln Tyr
145                 150

<210> SEQ ID NO 2
<211> LENGTH: 1997
<212> TYPE: DNA
<213> ORGANISM: Artificial
<220> FEATURE:
<223> OTHER INFORMATION: CsgA gene verification region
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (1981)..(1986)
<223> OTHER INFORMATION: n is a, c, g, or t
<220> FEATURE:
<221> NAME/KEY: misc_feature
<222> LOCATION: (1989)..(1997)
<223> OTHER INFORMATION: n is a, c, g, or t

<400> SEQUENCE: 2
nnnnnnnnnc gcancaganc nttctctccn ggttcntctt atgctcgata tttcaacaaa    60
ttaagacttt tctgaagagg gcagccattg ttgtgataaa tgaagtgact gtccatcaga   120
aacagtaaca actattttca cccgatcgtc cggggaaata tttaaactca acttcgtcaa   180
agcaatgggt tgattagcag gcaatgagag ggtcttttct tgcttcgtct gactttgccc   240
tgaactgcct tcgcgcaggg acaatatttg tactctgcac agacaagatt gagtaagagt   300
gacttcagga ataatggtgt acatatcccc ttgctgggtc gtattaaagg ttatctgact   360
ggaaagtgcc gcaaggagta ataacgcatt catattcttc tcccgaaaaa aaacagggct   420
tgcgccgtgt aggctggagc tgcttcgaag ttcctatact ttctagagaa taggaacttc   480
ggaataggaa cttcatttaa atggcgcgcc ttacgccccg ccctgccact catcgcagta   540
ctgttgtatt cattaagcat ctgccgacat ggaagccatc acaaacggca tgatgaacct   600
gaatcgccag cggcatcagc accttgtcgc cttgcgtata atatttgccc atggtgaaaa   660 cggggggcgaa gaagttgtcc atattggcca cgtttaaatc aaaactggtg aaactcaccc   720
agggattggc tgagacgaaa acatatttct caataaaccc tttagggaaa taggccaggt   780
tttcaccgta acacgccaca tcttgcgaat atatgtgtag aaactgccgg aaatcgtcgt   840
ggtattcact ccagagcgat gaaaacgttt cagtttgctc atggaaaacg gtgtaacaag   900
ggtgaacact atcccatatc accagctcac cgtctttcat tgccatacgt aattccggat   960
gagcattcat caggcgggca agaatgtgaa taaaggccgg ataaaacttg tgcttatttt  1020
```

-continued

```
tctttacggt ctttaaaaag gccgtaatat ccagctgaac ggtctggtta taggtacatt    1080
gagcaactga ctgaaatgcc tcaaaatgtt ctttacgatg ccattgggat atatcaacgg    1140
tggtatatcc agtgattttt ttctccattt tagcttcctt agctcctgaa aatctcgaca    1200
actcaaaaaa tacgcccggt agtgatctta tttcattatg gtgaaagttg gaacctctta    1260
cgtgccgatc aacgtctcat tttcgccaaa agttggccca gggcttcccg gtatcaacag    1320
ggacaccagg atttatttat tctgcgaagt gatcttccgt cacaggtagg cgcgccgaag    1380
ttcctatact ttctagagaa taggaacttc ggaataggaa ctaaggagga tattcatatg    1440
gaccatggct aattcccatg taaaaccccc atcggattga tttaaaagtc gaatggaaat    1500
taacgttgtg tcacgcgaat agccatttgc gactgtctct gcactacaat tgccgttttt    1560
tgagtaccat actgtgtaat atttgcttta ttaccagaac ctttctggat aatcatcgca    1620
gtattaccat aagcaccttg cgaaatactg gcatcgttgg cactgccgc ctgatcaata    1680 tatgcaaggt tataatctcc tgtctgatca atctttgccc agttgctact accttcttgc    1740
gcaacaaccg tcaaaagttt tgagcctccc tgccgtaact gagcactatt attagtccca    1800
gcttgaccaa ttatggctgc ctgattaaat gaagacttac tcaattcatt taccgcaaag    1860
ttatattctg aattagctaa atcataacct gctgcggctg caatcccagg cgcacccagt    1920
attgttaaca tcataaataa caatttgttt ttcatgttgt caccctggac ctggtcgtac    1980
nnnnnnaann nnnnnnn                                                   1997
```

<210> SEQ ID NO 3
<211> LENGTH: 19
<212> TYPE: PRT
<213> ORGANISM: Artificial
<220> FEATURE:
<223> OTHER INFORMATION: linker
<220> FEATURE:
<221> NAME/KEY: misc_feature
<222> LOCATION: (16)..(19)
<223> OTHER INFORMATION: Xaa can be any naturally occurring amino acid

<400> SEQUENCE: 3

Gly Gly Ser Gly Gly Ser Gly Gly Ser Gly Gly Ser Gly Gly Ser Xaa
1               5                   10                  15

Xaa Xaa Xaa

<210> SEQ ID NO 4
<211> LENGTH: 4
<212> TYPE: PRT
<213> ORGANISM: Artificial
<220> FEATURE:
<223> OTHER INFORMATION: linker

<400> SEQUENCE: 4

Gly Gly Gly Ser
1

<210> SEQ ID NO 5
<211> LENGTH: 12
<212> TYPE: PRT
<213> ORGANISM: Artificial
<220> FEATURE:
<223> OTHER INFORMATION: linker

<400> SEQUENCE: 5

Gly Gly Gly Ser Gly Gly Gly Ser Gly Gly Gly Ser
1               5                   10

<210> SEQ ID NO 6
<211> LENGTH: 24
<212> TYPE: PRT
<213> ORGANISM: Artificial
<220> FEATURE:
<223> OTHER INFORMATION: linker

<400> SEQUENCE: 6

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 7
<211> LENGTH: 48
<212> TYPE: PRT
<213> ORGANISM: Artificial
<220> FEATURE:
<223> OTHER INFORMATION: linker

<400> SEQUENCE: 7

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

<210> SEQ ID NO 8
<211> LENGTH: 12
<212> TYPE: PRT
<213> ORGANISM: Artificial
<220> FEATURE:
<223> OTHER INFORMATION: linker

<400> SEQUENCE: 8

Pro Pro Pro Pro Pro Pro Pro Pro Pro Pro Pro Pro
1               5                   10

<210> SEQ ID NO 9
<211> LENGTH: 24
<212> TYPE: PRT
<213> ORGANISM: Artificial
<220> FEATURE:
<223> OTHER INFORMATION: linker

<400> SEQUENCE: 9

Pro Pro Pro Pro Pro Pro Pro Pro Pro Pro Pro Pro Pro Pro Pro Pro
1               5                   10                  15

Pro Pro Pro Pro Pro Pro Pro Pro
            20

<210> SEQ ID NO 10
<211> LENGTH: 15
<212> TYPE: PRT
<213> ORGANISM: Artificial
<220> FEATURE:
<223> OTHER INFORMATION: linker

<400> SEQUENCE: 10

Glu Ala Ala Ala Lys Glu Ala Ala Ala Lys Glu Ala Ala Ala Lys
1               5                   10                  15

<210> SEQ ID NO 11

<211> LENGTH: 45
<212> TYPE: PRT
<213> ORGANISM: Artificial
<220> FEATURE:
<223> OTHER INFORMATION: linker

<400> SEQUENCE: 11

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
                20                  25                  30

Ala Ala Lys Glu Ala Ala Ala Lys Glu Ala Ala Ala Lys
            35                  40                  45

<210> SEQ ID NO 12
<211> LENGTH: 80
<212> TYPE: PRT
<213> ORGANISM: Artificial
<220> FEATURE:
<223> OTHER INFORMATION: linker

<400> SEQUENCE: 12

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser Gly Gly Gly Ser Gly Gly Gly Ser
            35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

<210> SEQ ID NO 13
<211> LENGTH: 30
<212> TYPE: PRT
<213> ORGANISM: Artificial
<220> FEATURE:
<223> OTHER INFORMATION: linker_nucleotides 1 to 29 may be absent

<400> SEQUENCE: 13

Pro Pro Pro Pro Pro Pro Pro Pro Pro Pro Pro Pro Pro Pro Pro Pro
1               5                   10                  15

Pro Pro Pro Pro Pro Pro Pro Pro Pro Pro Pro Pro Pro Pro
                20                  25                  30

<210> SEQ ID NO 14
<211> LENGTH: 5
<212> TYPE: PRT
<213> ORGANISM: Artificial
<220> FEATURE:
<223> OTHER INFORMATION: linker

<400> SEQUENCE: 14

Glu Ala Ala Ala Lys
1               5

<210> SEQ ID NO 15
<211> LENGTH: 75
<212> TYPE: PRT
<213> ORGANISM: Artificial
<220> FEATURE:
<223> OTHER INFORMATION: linker_EAAAK may be absent 1 to 14 times

```
<400> SEQUENCE: 15

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
                20                  25                  30

Ala Ala Lys Glu Ala Ala Ala Lys Glu Ala Ala Ala Lys Glu Ala Ala
            35                  40                  45

Ala Lys Glu Ala Ala Ala Lys Glu Ala Ala Ala Lys Glu Ala Ala Ala
        50                  55                  60

Lys Glu Ala Ala Ala Lys Glu Ala Ala Ala Lys
65                  70                  75

<210> SEQ ID NO 16
<211> LENGTH: 48
<212> TYPE: PRT
<213> ORGANISM: Artificial
<220> FEATURE:
<223> OTHER INFORMATION: linker

<400> SEQUENCE: 16

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser Gly Gly Gly Ser Gly Gly Gly Ser
            35                  40                  45

<210> SEQ ID NO 17
<211> LENGTH: 24
<212> TYPE: PRT
<213> ORGANISM: Artificial
<220> FEATURE:
<223> OTHER INFORMATION: linker

<400> SEQUENCE: 17

Pro Pro Pro Pro Pro Pro Pro Pro Pro Pro Pro Pro Pro Pro Pro Pro
1               5                   10                  15

Pro Pro Pro Pro Pro Pro Pro Pro
                20

<210> SEQ ID NO 18
<211> LENGTH: 45
<212> TYPE: PRT
<213> ORGANISM: Artificial
<220> FEATURE:
<223> OTHER INFORMATION: linker

<400> SEQUENCE: 18

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
                20                  25                  30

Ala Ala Lys Glu Ala Ala Ala Lys Glu Ala Ala Ala Lys
            35                  40                  45

<210> SEQ ID NO 19
<211> LENGTH: 7
<212> TYPE: PRT
<213> ORGANISM: Artificial
<220> FEATURE:
<223> OTHER INFORMATION: binding domain
```

<400> SEQUENCE: 19

Val His Leu Gly Tyr Ala Thr
1               5

<210> SEQ ID NO 20
<211> LENGTH: 12
<212> TYPE: PRT
<213> ORGANISM: Artificial
<220> FEATURE:
<223> OTHER INFORMATION: binding domain

<400> SEQUENCE: 20

Leu Glu Thr Thr Cys Ala Ser Leu Cys Tyr Pro Ser
1               5                   10

<210> SEQ ID NO 21
<211> LENGTH: 7
<212> TYPE: PRT
<213> ORGANISM: Artificial
<220> FEATURE:
<223> OTHER INFORMATION: binding domain

<400> SEQUENCE: 21

Val Arg Pro Met Pro Leu Gln
1               5

<210> SEQ ID NO 22
<211> LENGTH: 12
<212> TYPE: PRT
<213> ORGANISM: Artificial
<220> FEATURE:
<223> OTHER INFORMATION: binding domain

<400> SEQUENCE: 22

Leu Thr His Pro Gln Asp Ser Pro Pro Ala Ser Ala
1               5                   10

<210> SEQ ID NO 23
<211> LENGTH: 106
<212> TYPE: PRT
<213> ORGANISM: Artificial
<220> FEATURE:
<223> OTHER INFORMATION: binding domain

<400> SEQUENCE: 23

Glu Lys Pro Ala Ala Cys Arg Cys Ser Arg Gln Asp Pro Lys Asn Arg
1               5                   10                  15

Val Asn Cys Gly Phe Pro Gly Ile Thr Ser Asp Gln Cys Phe Thr Ser
                20                  25                  30

Gly Cys Cys Phe Asp Ser Gln Val Pro Gly Val Pro Trp Cys Phe Lys
        35                  40                  45

Pro Leu Pro Ala Gln Glu Ser Glu Glu Cys Val Met Gln Val Ser Ala
    50                  55                  60

Arg Lys Asn Cys Gly Tyr Pro Gly Ile Ser Pro Glu Asp Cys Ala Ala
65                  70                  75                  80

Arg Asn Cys Cys Phe Ser Asp Thr Ile Pro Glu Val Pro Trp Cys Phe
                85                  90                  95

Phe Pro Met Ser Val Glu Asp Cys His Tyr
                100                 105

<210> SEQ ID NO 24
<211> LENGTH: 59
<212> TYPE: PRT

<213> ORGANISM: Artificial
<220> FEATURE:
<223> OTHER INFORMATION: binding domain

<400> SEQUENCE: 24

Glu Glu Tyr Val Gly Leu Ser Ala Asn Gln Cys Ala Val Pro Ala Lys
1               5                   10                  15

Asp Arg Val Asp Cys Gly Tyr Pro His Val Thr Pro Lys Glu Cys Asn
            20                  25                  30

Asn Arg Gly Cys Cys Phe Asp Ser Arg Ile Pro Gly Val Pro Trp Cys
        35                  40                  45

Phe Lys Pro Leu Gln Glu Ala Glu Cys Thr Phe
    50                  55

<210> SEQ ID NO 25
<211> LENGTH: 12
<212> TYPE: PRT
<213> ORGANISM: Artificial
<220> FEATURE:
<223> OTHER INFORMATION: peptide domain

<400> SEQUENCE: 25

Leu Thr His Pro Gln Asp Ser Pro Pro Ala Ser Ala
1               5                   10

<210> SEQ ID NO 26
<211> LENGTH: 7
<212> TYPE: PRT
<213> ORGANISM: Artificial
<220> FEATURE:
<223> OTHER INFORMATION: peptide domain

<400> SEQUENCE: 26

Val His Leu Gly Tyr Ala Thr
1               5

<210> SEQ ID NO 27
<211> LENGTH: 12
<212> TYPE: PRT
<213> ORGANISM: Artificial
<220> FEATURE:
<223> OTHER INFORMATION: peptide domain

<400> SEQUENCE: 27

Leu Glu Thr Thr Cys Ala Ser Leu Cys Tyr Pro Ser
1               5                   10

<210> SEQ ID NO 28
<211> LENGTH: 7
<212> TYPE: PRT
<213> ORGANISM: Artificial
<220> FEATURE:
<223> OTHER INFORMATION: peptide domain

<400> SEQUENCE: 28

Val Arg Pro Met Pro Leu Gln
1               5

<210> SEQ ID NO 29
<211> LENGTH: 5
<212> TYPE: PRT
<213> ORGANISM: Artificial
<220> FEATURE:
<223> OTHER INFORMATION: proline sequence
<220> FEATURE:
<221> NAME/KEY: misc_feature

```
<222> LOCATION: (3)..(3)
<223> OTHER INFORMATION: Xaa can be any naturally occurring amino acid

<400> SEQUENCE: 29

Leu Pro Xaa Thr Gly
1               5

<210> SEQ ID NO 30
<211> LENGTH: 19
<212> TYPE: PRT
<213> ORGANISM: Artificial
<220> FEATURE:
<223> OTHER INFORMATION: linker_GGS repeat may be absent 3 to 4 times
<220> FEATURE:
<221> NAME/KEY: misc_feature
<222> LOCATION: (16)..(19)
<223> OTHER INFORMATION: Xaa can be any naturally occurring amino acid

<400> SEQUENCE: 30

Gly Gly Ser Gly Gly Ser Gly Gly Ser Gly Gly Ser Gly Gly Ser Xaa
1               5                   10                  15

Xaa Xaa Xaa

<210> SEQ ID NO 31
<211> LENGTH: 43
<212> TYPE: PRT
<213> ORGANISM: Artificial
<220> FEATURE:
<223> OTHER INFORMATION: binding domain

<400> SEQUENCE: 31

Ser Lys Trp Gln His Gln Gln Asp Ser Cys Arg Lys Gln Leu Gln Gly
1               5                   10                  15

Val Asn Leu Thr Pro Cys Glu Lys His Ile Met Glu Lys Ile Gln Gly
            20                  25                  30

Arg Gly Asp Asp Asp Asp Asp Asp Asp Asp Asp
        35                  40

<210> SEQ ID NO 32
<211> LENGTH: 134
<212> TYPE: PRT
<213> ORGANISM: Artificial
<220> FEATURE:
<223> OTHER INFORMATION: binding domain

<400> SEQUENCE: 32

Met Met Met Pro Ala Asn Tyr Ser Val Ile Ala Glu Asn Glu Met Thr
1               5                   10                  15

Tyr Val Asn Gly Gly Ala Asn Phe Ile Asp Ala Ile Gly Ala Val Thr
            20                  25                  30

Ala Pro Ile Trp Thr Leu Asp Asn Val Lys Thr Phe Asn Thr Asn Ile
        35                  40                  45

Val Thr Leu Val Gly Asn Thr Phe Leu Gln Ser Thr Ile Asn Arg Thr
    50                  55                  60

Ile Val Leu Phe Ser Gly Asn Thr Thr Trp Lys Glu Val Gly Asn Ile
65              70                  75                  80

Gly Lys Asn Leu Phe Gly Thr Asn Val Lys Gly Asn Pro Ile Glu Lys
                85                  90                  95

Asn Asn Phe Gly Asp Tyr Ala Met Asn Ala Leu Gly Ile Ala Ala Ala
            100                 105                 110

Val Tyr Asn Leu Gly Val Ala Pro Thr Lys Asn Thr Val Lys Glu Thr
        115                 120                 125
```

```
Glu Val Lys Phe Thr Val
    130

<210> SEQ ID NO 33
<211> LENGTH: 18
<212> TYPE: PRT
<213> ORGANISM: Artificial
<220> FEATURE:
<223> OTHER INFORMATION: binding peptide

<400> SEQUENCE: 33

Asp Trp Phe Lys Ala Phe Tyr Asp Lys Val Ala Glu Lys Phe Lys Glu
1               5                   10                  15

Ala Phe

<210> SEQ ID NO 34
<211> LENGTH: 12
<212> TYPE: PRT
<213> ORGANISM: Artificial
<220> FEATURE:
<223> OTHER INFORMATION: binding peptide

<400> SEQUENCE: 34

Gly Gly Ala Val Val Thr Gly Val Thr Ala Val Ala
1               5                   10

<210> SEQ ID NO 35
<211> LENGTH: 12
<212> TYPE: PRT
<213> ORGANISM: Artificial
<220> FEATURE:
<223> OTHER INFORMATION: binding peptide

<400> SEQUENCE: 35

Gly Gly Ala Val Val Thr Gly Val Thr Ala Val Ala
1               5                   10

<210> SEQ ID NO 36
<211> LENGTH: 12
<212> TYPE: PRT
<213> ORGANISM: Artificial
<220> FEATURE:
<223> OTHER INFORMATION: binding peptide

<400> SEQUENCE: 36

Leu Thr His Pro Gln Asp Ser Pro Pro Ala Ser Ala
1               5                   10

<210> SEQ ID NO 37
<211> LENGTH: 220
<212> TYPE: PRT
<213> ORGANISM: Artificial
<220> FEATURE:
<223> OTHER INFORMATION: binding peptide

<400> SEQUENCE: 37

Leu Val Val Ala Thr Asp Thr Ala Phe Val Pro Phe Glu Phe Lys Gln
1               5                   10                  15

Gly Asp Lys Tyr Val Gly Phe Asp Val Asp Leu Trp Ala Ala Ile Ala
            20                  25                  30

Lys Glu Leu Lys Leu Asp Tyr Glu Leu Lys Pro Met Asp Phe Ser Gly
        35                  40                  45

Ile Ile Pro Ala Leu Gln Thr Lys Asn Val Asp Ala Leu Ala Gly Ile
    50                  55                  60
```

```
Thr Ile Thr Asp Glu Arg Lys Lys Ala Ile Asp Phe Ser Asp Gly Tyr
 65                  70                  75                  80

Tyr Lys Ser Gly Leu Leu Val Met Val Lys Ala Asn Asn Asn Asp Val
                 85                  90                  95

Lys Ser Val Lys Asp Leu Asp Gly Lys Val Val Ala Val Lys Ser Gly
            100                 105                 110

Thr Gly Ser Val Asp Tyr Ala Lys Ala Asn Ile Lys Thr Lys Asp Leu
            115                 120                 125

Arg Gln Phe Pro Asn Ile Asp Asn Ala Tyr Met Glu Leu Gly Thr Asn
        130                 135                 140

Arg Ala Asp Ala Val Leu His Asp Thr Pro Asn Ile Leu Tyr Phe Ile
145                 150                 155                 160

Lys Thr Ala Gly Asn Gly Gln Phe Lys Ala Val Gly Asp Ser Leu Glu
                165                 170                 175

Ala Gln Tyr Gly Ile Ala Phe Pro Lys Gly Ser Asp Glu Leu Arg Asp
            180                 185                 190

Lys Val Asn Gly Ala Leu Lys Thr Leu Arg Glu Asn Gly Thr Tyr Asn
        195                 200                 205

Glu Ile Tyr Lys Lys Trp Phe Gly Thr Glu Pro Lys
    210                 215                 220

<210> SEQ ID NO 38
<211> LENGTH: 60
<212> TYPE: PRT
<213> ORGANISM: Artificial
<220> FEATURE:
<223> OTHER INFORMATION: binding domain

<400> SEQUENCE: 38

Glu Ala Gln Thr Glu Thr Cys Thr Val Ala Pro Arg Glu Arg Gln Asn
1               5                   10                  15

Cys Gly Phe Pro Gly Val Thr Pro Ser Gln Cys Ala Asn Lys Gly Cys
            20                  25                  30

Cys Phe Asp Asp Thr Val Arg Gly Val Pro Trp Cys Phe Tyr Pro Asn
        35                  40                  45

Thr Ile Asp Val Pro Pro Glu Glu Cys Glu Phe
    50                  55                  60

<210> SEQ ID NO 39
<211> LENGTH: 48
<212> TYPE: PRT
<213> ORGANISM: Artificial
<220> FEATURE:
<223> OTHER INFORMATION: Fusion domain linker_GGGS repeat can be 48, 36,
      or 24 AA

<400> SEQUENCE: 39

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

<210> SEQ ID NO 40
<211> LENGTH: 36
<212> TYPE: PRT
<213> ORGANISM: Artificial
<220> FEATURE:
```

```
<223> OTHER INFORMATION: linker_GGGS repeat can be 36, 24, or 12 AA

<400> SEQUENCE: 40

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser
        35
```